(12) United States Patent
Kónya et al.

(10) Patent No.: US 6,994,717 B2
(45) Date of Patent: Feb. 7, 2006

(54) OCCLUSION METHOD AND APPARATUS

(75) Inventors: András Kónya, Houston, TX (US); Sidney Wallace, Houston, TX (US); Kenneth C. Wright, Houston, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 264 days.

(21) Appl. No.: 10/119,379

(22) Filed: Apr. 9, 2002

(65) Prior Publication Data

US 2002/0156499 A1 Oct. 24, 2002

Related U.S. Application Data

(62) Division of application No. 09/263,382, filed on Mar. 5, 1999, now Pat. No. 6,368,338.

(51) Int. Cl.
*A61M 29/00* (2006.01)

(52) U.S. Cl. ...................................................... 606/200
(58) Field of Classification Search ............... 606/200, 606/194, 195, 157, 158; 623/1.13, 2.2–2.37; 128/843

See application file for complete search history.

(56) References Cited

U.S. PATENT DOCUMENTS

| | | | |
|---|---|---|---|
| 3,540,431 A | 11/1970 | Mobim-Uddim | |
| 3,794,041 A | 2/1974 | Frei et al. | |
| 3,868,956 A | 3/1975 | Alfidi et al. | |
| 4,365,632 A | 12/1982 | Kortum | |
| 4,425,908 A | 1/1984 | Simon | |
| 4,447,227 A | 5/1984 | Kotsanis | |
| 4,494,531 A | 1/1985 | Gianturco | |
| 4,512,338 A | 4/1985 | Balko et al. | |
| 4,619,246 A | 10/1986 | Mølgaard-Nielsen et al. | |
| 4,638,803 A | 1/1987 | Rand | |
| 4,650,466 A | 3/1987 | Luther | |

(Continued)

OTHER PUBLICATIONS

Beathard, "Mechanical versus pharmacomechanical thrombolysis for the treatment of thrombosed dialysis access grafts," *Kidney Int.*, 45:1401–1406, 1994.

Beathard et al., "Mechanical thrombolysis for the treatment of thrombosed hemodialysis access grafts," *Radiology*, 200:711–716, 1996.

(Continued)

*Primary Examiner*—(Jackie) Tan-Uyen T. Ho
(74) *Attorney, Agent, or Firm*—Fulbright & Jaworski, LLP

(57) ABSTRACT

An occlusion method and apparatus. The occluder includes elastically deformable members and a jacket. The elastically deformable members are secured in spaced relation and extend in arcuate conformation therebetween. The jacket covers at least a portion of the elastically deformable members. The elastically deformable members are configured to become compressed upon application of a force and to recover the arcuate conformation upon removal of the fore to occlude a site.

14 Claims, 14 Drawing Sheets

U.S. PATENT DOCUMENTS

| | | | |
|---|---|---|---|
| 4,832,055 A | 5/1989 | Palestrant | |
| 4,921,484 A | 5/1990 | Hillstead | |
| 4,957,501 A | 9/1990 | Lahille et al. | |
| 4,994,069 A | 2/1991 | Ritchart et al. | |
| 4,997,435 A | 3/1991 | Demeter | |
| 5,053,008 A | 10/1991 | Bajaj | |
| 5,071,407 A | 12/1991 | Termin et al. | |
| 5,104,404 A | 4/1992 | Wolff | |
| 5,108,407 A | 4/1992 | Geremia et al. | |
| 5,108,419 A | 4/1992 | Reger et al. | |
| 5,133,733 A | 7/1992 | Rasmussen et al. | |
| 5,217,484 A | 6/1993 | Marks | |
| 5,226,911 A | 7/1993 | Chee et al. | |
| 5,256,146 A | 10/1993 | Ensminger et al. | |
| 5,263,964 A | 11/1993 | Purdy | |
| 5,334,210 A | 8/1994 | Gianturco | |
| 5,350,398 A | 9/1994 | Pavcnik et al. | |
| 5,370,657 A | 12/1994 | Irie | |
| 5,375,612 A | 12/1994 | Cottenceau et al. | |
| 5,443,478 A | 8/1995 | Purdy | |
| 5,490,859 A | 2/1996 | Mische et al. | |
| 5,527,338 A | 6/1996 | Purdy | |
| 5,531,788 A | 7/1996 | Dibie et al. | |
| 5,669,933 A | 9/1997 | Simon et al. | |
| 5,693,067 A | 12/1997 | Purdy | |
| 5,709,704 A | 1/1998 | Nott et al. | |
| 5,720,764 A | 2/1998 | Naderlinger | |
| 5,766,219 A | 6/1998 | Horton | |
| 5,836,968 A | 11/1998 | Simon et al. | |
| 5,836,969 A | 11/1998 | Kim et al. | |
| 5,868,708 A | 2/1999 | Hart et al. | |
| 5,895,410 A | 4/1999 | Forber et al. | |
| 5,911,734 A | 6/1999 | Tsugita et al. | |
| 5,980,554 A * | 11/1999 | Lenker et al. | 606/198 |
| 6,010,517 A * | 1/2000 | Baccaro | 606/151 |
| 6,146,396 A | 11/2000 | Konya et al. | |
| 6,152,144 A | 11/2000 | Lesh et al. | |
| 6,428,558 B1 * | 8/2002 | Jones et al. | 606/200 |
| 6,605,111 B2 * | 8/2003 | Bose et al. | 623/1.18 |

OTHER PUBLICATIONS

Ben–Menachem et al, "Hemorrhage associated with pelvic fractures: causes, diagnosis, and emergent management," *AJR*, 157:1005–1014, 1991.

Bing et al, "Percutaneous ureteral occlusion with use of Gianturco coils and gelatin sponge, Part I. Swine model" *JVIR*, 3:313–317, 1992(a).

Bing et al, "Percutaneous ureteral occlusion with use of Gianturco coils and gelatin sponge, Part II. Clinical Experience," *JVIR*, 3:319–321, 1992(b).

Cambier et al, "Percutaneous closure of the small (<2.5 mm) patent ductus arteriosus using coil embolization," *Am. J. Cardiol.*, 69:815–816, 1992.

Castleman et al, "Biocompatibility of nitinol alloy as an implant material," *J. Biomed. Mater. Res.*, 10:695–731, 1976.

Dutton et al., "Pulmonary arteriovenous malformations: results of treatment with coil embolization in 53 patients," *AJR*, 165:1119–1125, 1995.

Feldman et al., "Vascular access morbidity in the US," *Kidney Int.*, 43:1091–1096, 1993.

Filcard International, "Instructions for use filcard temporary filter," 6 pages.

Furuse et al, "Hepatocellular carcinoma with portal vein tumor thrombus: embolization of arterioportal shunts," *Radiology*, 204:787–790, 1997.

Baxter Healthcare Corporation, Vascular Systems Division brochure, 3 pages.

Gianturco et al, "Mechanical device for arterial occlusion," *AJR*, 124:428–435, 1975.

Gray, "Percutaneous intervention for permanent hemodialysis access: A review," *JVIR*, 8:313–327, 1997.

Grifka et al, "Transcatheter patent ductus arteriosus closure in an infant using the Gianturco Grifka vascular occlusion device," *Am. J. Cardiol.*, 78:721–723, 1996.

Guglielmi et al, "Highflow, small–hole arteriovenous fistulas: treatment with electrodetachable coils," *AJNR*, 16:325–328, 1995.

Gunther et al., "Transrenal ureteral occlusion with a detachable balloon," *Radiology*, 142: 521–523, 1982.

Hendrickx et al, "Long–term survival after embolization of potentially lethal bleeding malignant pelvic turnouts," *Br. J. Radial.*, 68:1336–1343, 1995.

Hijazi and Geggel, "Results of anterograde transcatheter closure of patent ductus arteriosus using single or multiple Gianturco coils," *Am. J. Cardiol.*, 74:925–929, 1994.

Hijazi and Geggel, "Transcatheter closure of patent ductus arteriosus using coils," *Am. J. Cardiol.*, 79:1279–1280, 1997.

Hosking et al, "Transcatheter occlusion of the persistently patent ductus arteriosus," *Circulation*, 84:2313–2317, 1991.

Kinney et al., "Pulmonary emboli occurring with pulse–spray pharmacomechanical thrombolysis of clotted dialysis grafts with urokinase or heparinized saline," *JVIR Supplement*, 10(2) Part 2, p. 272–273, Feb., 1999.

Kónya et al, "Anchoring coil embolization in a high–flow arterial model," *JVIR*, 9:249–254, 1998.

Kónya et al., "Prelminary results with a new vascular occlusion device in an arterial model," *JVIR Supplement*, 9(1) Part 2, p. 213, Jan.–Feb., 1998.

Krichenko et al, "Angiographic classification of the isolated, persistently patent ductus arteriosus and implications for percutaneous catheter occlusion," *Am. J. Cardiol.*, 63:877–880, 1989.

Kumpe, "Fibrinolysis and angioplasty in the treatment of failed dialysis access sites," *JVIR Supplement*, 8(1) Part 2, p. 120–126, Jan.–Feb., 1997.

Latson, "Residual shunts after transcatheter closure of patent ductus arteriosus," *Circulation*, 84:2591–2593, 1991.

Lazzano et al., "Modified use of the Arrow–Trerotola percutaneous thrombolytic device for the treatment of thrombosed dialysis graft," *JVIR Supplement*, 10(2) Part 2, p. 233–234, Feb., 1999.

Liu and Stice, "Shape memory alloys and their applications," *J. Appl. Manufact. Sys.*, 3:65–72, 1990.

Lloyd et al, "Transcatheter occlusion of patent ductus arteriosus with Gianturco coils," *Circulation*, 88:1412–1420, 1993.

Magal et al, "A new device for transcatheter closure of patent ductus arteriosus: a feasibility study in dogs," *Invest. Radiol.*, 24:272–276, 1989.

Mailloux et al., "Survival estimates for 683 patients starting dialysis from 1970 through 1989: Identification of risk factors for survival," *Clin. Nephrol.*, 42:127–135, 1994.

Marks et al, "A mechanically detachable coil for the treatment of aneurysms and occlusion of blood vessels," *AJNR*, 15:821–827, 1994.

Masura et al, "Catheter closure of moderate to large sized patent ductus arteriosus using the new Amplatz duct occluder: immediate and short term results," *J. Am. Coll. Cardiol.*, 31:878–882, 1998.

Middlebrook et al., "Thrombosed hemodialysis grafts: percutaneous mechanical balloon declotting versus thrombolysis," *Radiology*, 196:73–77, 1995.

Nancarrow et al, "Stability of coil emboli: an in vitro study," *Cardiovasc. Intervent. Radiol.*, 10:226–229, 1987.

O'Halpin et al, "Therapeutic arterial embolization: report of five years' experience," *Clin. Radiol.*, 354:85–93, 1984.

Papanicoulau et al., "Percutaneous occlusion of ureteral leaks and fistulae using nondetachable balloons," *Urol. Radial.*, 7:28–31, 1985.

Pozza et al, "Transcatheter occlusion of patent ductus arteriosus using a newly developed self–expanding device: evaluation in a canine model," *Invest. Radiol.*, 30:104–109, 1995.

Punekar et al, "Post–surgical recurrent varicocele: efficacy of internal spermatic venography and steel–coil embolization," *Br. J. Urol.*, 77:12–128, 1996.

Rashkind et al, "Nonsurgical closure of patent ductus arteriosus: clinical application of the Rushkind PDA occluder system," *Circulation*, 75:583–592, 1987.

Reidy and Qureshi, "Interlocking detachable platinum coils, a controlled embolization device: early clinical experience," *Cardiovasc. Intervent. Radiol.*, 19:85–90, 1996.

Sagara et al, "Recanalization after coil embolotherapy of pulmonary arteriovenous malformations: study of long term outcome and mechanism for recanalization," *AJR*, 170:727–730, 1998.

Sanchez et al., "Urinary diversion by using a percutaneous ureteral occlusion device," *AJR*, 150; 1069–1070, 1988.

Schild et al, "Effectiveness of platinum wire microcoils for venous occlusion: a study on patients treated for venogenic impotence," *Cardiovasc. Intervent. Radiol.*, 17:170–172, 1994.

Schmitz–Rode et al, "Self–expandable spindle for transcatheter vascular occlusion: in vivo experiments," *Radiology*, 188:95–100, 1993.

Schwartz et al, "Effectiveness of transcatheter embolization in the control of hepatic vascular injuries," *JVIR*, 4:359–365, 1993.

Selby Jr., "Interventional radiology of trauma," *Radiol. clin. N. Am.*, 30:427–439, 1992.

Sharaffuddin et al, "Repositionable vascular occluder: experimental comparison with standard Gianturco coils," *JVIR*, 7:695–703, 1996.

Sharafuddin et al, "Experimental evaluation of a new self expanding patent ductus arteriosus occluder in a canine model," *JVIR*, 7:877–887, 1996.

Sommer et al, "Use of preformed nitinol snare to improve transcatheter coil delivery in occlusion of patent ductus arteriosus," *Am. J. Cardiol.*, 74:836–839, 1994.

Teitelbaum et al, "Microcatheter embolization of nonneurologic traumatic vascular lesions," *JVIR*, 4:149–154, 1993.

Tometzki et al., "Transcatheter occlusion of the patent ductus arteriosus with Cook detachable coils," *Heart*, 76:531–535, 1996.

"Transcatheter occlusion of persistent arterial duct." Report of the European Registry, Lancet, 340:1062–1066, 1992.

Trerotola et al., "Percutanous use of the Fogarty adherent clot catheter," *JVIR*, 6:578–580, 1995.

Trerotola et al., "Thrombosed hemodialysis access grafts: percutanenous mechanical declotting without urokinase," *Radiology*, 191:721–726, 1994.

Trerotola, "Mechanical thrombolysis of hemodialysis grafts," *JVIR Supplement*, 8(1) Part 2, pp. 126–130, Jan.–Feb., 1997.

Uflacker et al., "Treatment of thrombosed dialysis access grafts: randomized trial of surgical thrombectomy versus mechanical thrombectomy with the amplatz device," *JVIR*, 7:185–192, 1996.

Uzun et al, "Transcatheter occlusion of the arterial duct with Cook detachable coils: early experience," *Heart*, 76:269–273, 1996.

Vedantham et al, "Uterine artery embolization: an underused method of controlling pelvic hemorrhage," *Am. J. Obstet. Gynecol.*, 176:938–948, 1997.

Vorwerk et al., "Hydrodynamic thrombectomy of hemodialysis fistulas: First clinical results," *JVIR*, 5:813–821, 1994.

Wallace et al, "Arterial occlusion of pelvic bone tumors," *Cancer*, 43: 322–328, 1979.

Wessel et al, "Outpatient closure of the patent ductus arteriosus," *Circulation*, 77:1068–1071, 1988.

White et al, "Pulmonary arterivenous malformations: diagnosis and transcatheter embolotherapy," *JVIR*, 7:787–804, 1996.

Zubillaga et al, "Endovascular occlusion of intracranial aneurysms with electrically detachable coils: correlation of aneurysm neck size and treatment results," *AJNR*, 15:815–820, 1994.

Levey et al., "Safety and efficacy of transcatheter embolization of axillary and shoulder arterial injuries," *JVIR*, 2:99–104, 1991.

* cited by examiner

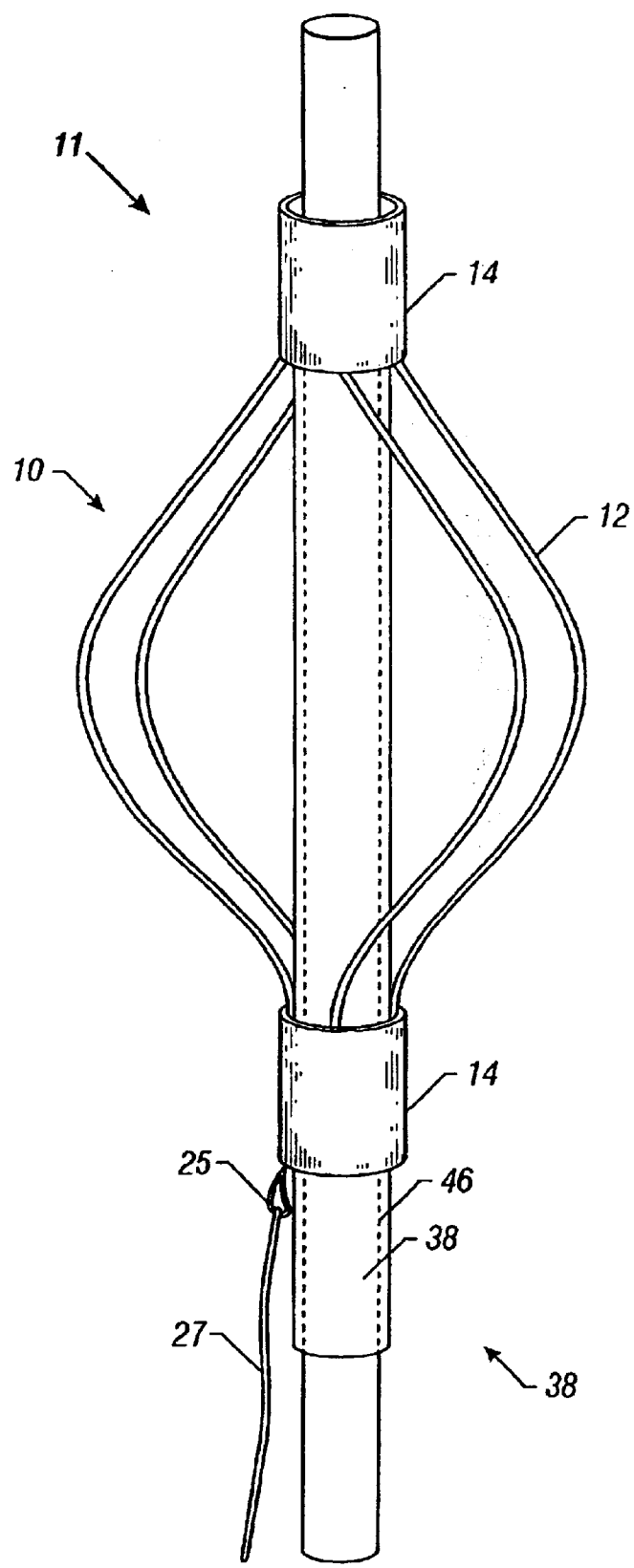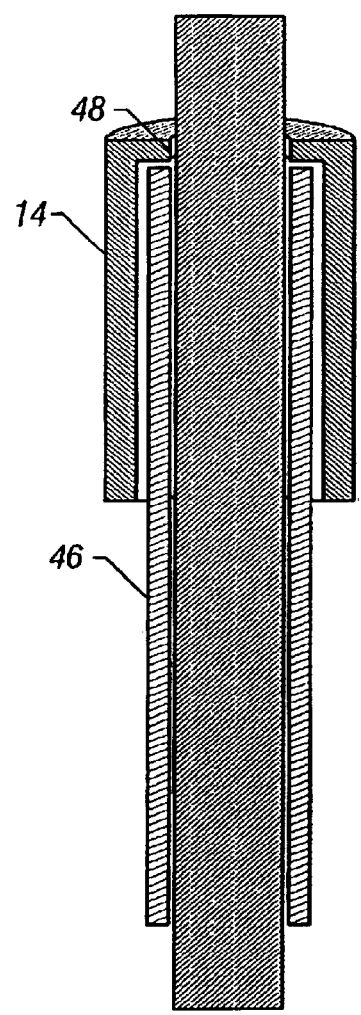
FIG. 17
FIG. 18

OCCLUSION METHOD AND APPARATUS

This application is a divisional application of, and claims priority to, U.S. patent application Ser. No. 09/263,382, filed Mar. 5, 1999 and issued as U.S. Pat. No. 6,368,338.

BACKGROUND OF THE INVENTION

1. Field of the Invention

The present invention relates generally to the field of occlusion of vessels and other tubular structures in the body. More particularly, it concerns a method and apparatus for repositionable, self-anchoring occlusion including vascular and ureter occlusion.

2. Description of Related Art

Percutaneous occlusion techniques have become indispensable tools in minimally invasive management of a wide range of pathological conditions. Use of permanent mechanical occlusion devices has been shown to be equivalent to that of surgical ligation. The Gianturco-Wallace stainless steel coil (Cook Inc., Bloomington, Ind.) has been the most widely used permanent, expandable intravascular occlusion device for transcatheter delivery (Gianturco et al., 1975). The use of detachable balloons, another effective mechanical occlusion technique, has been largely abandoned in the United States because of safety concerns (Sharaffiuddin et al., 1996).

Percutaneous coil embolization has been shown to be advantageous over traditional surgical procedures in treatment of life threatening hemorrhage due to trauma or obstetric emergencies (Schwartz et al., 1993; Teitelbaum et al., 1993; Selby Jr., 1992; Levey et al., 1991; Ben-Menachem et al., 1991; Vedantham et al., 1997). Furthermore, coils have been used alone or in combination with microvascular embolic agents for the treatment of vascular fistulas and malformations, tumors, and varices (Wallace et al., 1979; Hendrickx et al., 1995; Furuse et al, 1997; White et al., 1996; Sagara et al., 1998; Punekar et al., 1996). During the last few years, the transcatheter closure of the patent ductus arteriosus (PDA) with coils has become a frequently used technique (Hijazi and Geggel, 1994; Hijazi and Geggl, 1997).

Although coil type occlusion devices have shown at least a degree of utility, they have a number of drawbacks that could be significant in some applications. Intravascular stability of the coils has been shown to be highly dependent on proper matching of coil diameter with the diameter of the target vessel (Nancarrow et al., 1987), and with the exception of small vessels, a single coil rarely results in a stable occlusive thrombus (Hijazi and Geggel, 1994). Moreover, a long vascular segment is often obliterated because of the frequent need for multiple coils and the coils often remain elongated within the vessel because their unconstrained diameter is larger than the vascular lumen. Furthermore, delayed recanalization rates of 37%–57% have been reported in humans within 1–3 months after initially successful coil embolization (Sagara et al., 1998; O'Halpin et al., 1984; Schild et al., 1994).

These and other drawbacks have inspired modifications in the design and technique of coil embolization. Recently, detachable microcoils and macrocoils with controlled delivery have been designed to achieve a more compact conglomerate of the coil and to prevent migration by allowing optimal positioning of the coil before release (Zubillaga et al., 1994; Guglielmi et al., 1995; Marks et al., 1994; Reidy and Qureshi, 1996; Uzun et al., 1996; Tometzki et al., 1996; Dutton et al., 1995). However, since optimal arrangement of the coil alone may not prevent migration in some cases, such as high flow conditions or venous placement, a coil anchoring system has been devised (Konya et al., 1998). Although an anchoring system may stabilize a coil conglomerate within the vasculature, significantly reducing or eliminating the possibility of coil migration, such a system may render the coil non-repositionable.

Several different non-coil devices have been designed to achieve a more stable, limited size plug with higher hemostatic efficiency particularly for transcatheter closure of larger vessels (Schmitz-Rode et al., 1993) and PDAs (Pozza et al., 1995; Magal et al., 1989; Grifka et al., 1996). Recently, initial clinical experiences with a new mesh PDA occluder have been reported (Sharafuddin et al., 1996; Masura et al., 1998). A similar self-expanding, repositionable quadruple-disc device constructed of a braided nitinol mesh and polyester fibers has been reported to be superior to standard Gianturco coils in experimental occlusion of mid-size arteries (Sharaffuddin et al., 1996).

Although such non-coil devices may be repositionable, they too exhibit drawbacks. For instance, the quadruple-disc device is several centimeters long in an elongated fashion, making difficult to keep the superselective position of the catheter tip during deployment. Although the mesh-PDA occluder has demonstrated utility, its proper placement requires a proper match both in size and shape between the occluder and the lesion to be occluded. A common disadvantage of both designs is that they lack guidewire compatibility. As a result, a delivery catheter must often be navigated to the site of occlusion first before an occluder may be loaded into the catheter and delivered through it. Another relative disadvantage of both devices is their cost of manufacturing.

Percutaneous catheter technique for permanent closure of isolated persistently patent ductus arteriosus (PDA) is now a treatment of choice among doctors, obviating open surgery. The configuration of the PDA varies considerably. A majority of PDAs tend to have a funnel or conical shape due to ductal smooth muscle constriction at the pulmonary artery insertion, although narrowings in the middle or aortic ends can be observed (Krichenko, 1989). That is the reason why not only the size, but also the configuration, of the lesion plays a significant role in selecting an appropriate occluding device. Except from the small caliber lesions (with a maximum diameter of 2.5 mm or 3.3 mm, respectively), where some authors have achieved successful closure of the PDA with Gianturco coils (Cambier, 1992; Lloyd, 1993; Sommer, 1994), Rashkind's "double umbrella" occluder is the most often used device for this purpose (Rashkind, 1987; Hosking, 1991; Latson, 1991; Wessel, 1988; Report of the European Registry, 1992). It is available in two sizes (with a diameter of 12 mm and 17 mm) which require a 8-P and 11-F delivery system, respectively.

In the majority of cases, the deployment of the traditional PDA device is performed from a femoral vein access (Report of the European Registry, 1992). Because of the size of the delivery sheath, such a device is not suitable for the treatment of patients with a body weight of less than 8 kg. Using even a larger umbrella, this procedure is not recommended for the treatment of the lesions with a diameter of 8 mm or above (Latson, 1991). About 80% of unselected patients with isolated PDA are candidates for the Rashkind device using the aforementioned criteria (Latson, 1991). With the Rashkind device, the proportion of patients with residual flow through the lesion fell from 76% immediately after implantation to 47% by the day after implantation and to 17% by a year after implantation (Report of the European Registry, 1992). According to some authors the residual flow carries a potential risk of infective endocarditis and should be avoided if possible. Its abolishment can be achieved by implantation of another device or surgery.

One of the main drawbacks of the Rashkind umbrella is that it is not suitable for occlusion of all types of PDA. Preferably, it is used to occlude short PDAs with relatively wide end-openings. Its two discs cover both the pulmonary and the aortic opening of the PDA. Longer PDA may hinder the discs to be positioned in the proper way, that is, parallel to each other, thereby deteriorating its self-anchoring. Another disadvantage of the umbrella is that the occluding capacity of the design depends exclusively on the thrombogenicity of the porous Dacron material, frequently resulting in partial and lengthy occlusion.

For the majority of patients with urinary leakage and/or fistlas (mainly due to tumor propagation to their ureters), the diversion of urine is currently performed by a percutaneous transrenal approach together with ureteral occlusion. Formerly, detachable and non detachable balloons were used for this purpose, but they did not cause satisfactory ureteral occlusion. Migration as well as deflation of the balloons occurred relatively frequently (Gunter, 1984; Papanicolau, 1985) leading to recurrence of the urine leakage. A silicone ureteral occluder was developed and used with only limited success because of device migration (Sanchez, 1988). This resulted in repositioning and consequent incomplete ureteral occlusion. It appears that the best results have been accomplished with Gianturco coils and Gelfoam embolization (Bing et al. 1992 a; ). Even with multiple coil placements, together with Gelfoam plugs, the ureteral occlusion may sometimes be achieved for only weeks or months, and was attributed mostly to the induced urothelial hyperplasia (Bing et al., 1992 b). Coil migration was frequently encountered in these studies. The lack of appropriate self-anchoring results in coil migration which eventually deteriorates the occlusive effect.

Problems pointed out in the foregoing are not intended to be exhaustive but rather are among many that tend to impair the effectiveness of previously known occlusion systems. Other noteworthy problems may also exist; however, those presented above should be sufficient to demonstrate that previous techniques appearing in the art have not been altogether satisfactory, particularly in providing fast, non-migratory, self-anchoring, repositionable occlusion.

SUMMARY OF THE INVENTION

In one aspect, the invention is an occluder including a elastically deformable members, and a jacket. As used herein, by "elastically deformable" it is meant that deformation is non-permanent and an original shape may be substantially recovered, or regained, upon the release of a force (which may be mechanical, electromagnetic, or any other type of force). By "substantially recovered", it is meant that recovery need not be such that the exact original shape may be regained. Rather, it is meant that some degree of plastic deformation may occur. In other words, recovery need not be total. The plurality of elastically deformable members are secured in spaced relation and extend in arcuate conformation therebetween. The plurality of elastically deformable members are operable to become compressed upon application of a force and to recover the arcuate conformation upon removal of the force. The jacket is in operable relation to the plurality of elastically deformable members and is configured to cover at least a portion of the plurality of elastically deformable members.

In other aspects, the plurality of elastically deformable members may be programmed with thermal memory. The plurality of elastically deformable members may be programmed with superelasticity. The plurality of elastically deformable members may be secured at their ends. The occluder may also include one or more anchors defined by one or more ends of the plurality of elastically deformable members. The occluder may also include a pair of clips in spaced relation for securing the plurality of elastically deformable members. At least one of the clips may be interdigitated. The occluder may also include an eye in operable relation to at least one of the clips. The jacket may include dacron. The jacket may include polyurethane. The plurality of elastically deformable members may include four or more nitinol wires. The occluder may also include an occluding agent enclosed within the jacket. The occluding agent may include one or more threads of polyester.

In another aspect, the invention is an occlusion system including an occluder and a delivery system. The occluder includes a pair of clips, a elastically deformable members, and a jacket. The pair of clips are configured in spaced relation. The plurality of elastically deformable wires are secured by the clips and extend in arcuate conformation therebetween. The plurality of elastically deformable wires are operable to become compressed upon application of a force and to recover the arcuate conformation upon removal of the force. The jacket is in operable relation to the plurality of elastically deformable wires and is configured to cover at least a portion of the plurality of elastically deformable wires. The delivery system includes a guiding catheter and a pushing catheter. The guiding catheter is configured to receive the occluder. The guiding catheter compresses and guides the plurality of elastically deformable wires. The pushing catheter is configured to engage at least one of the pair of clips to slide the occluder relative to the guiding catheter.

In other aspects, the plurality of elastically deformable wires may include four, five, or six nitinol wires. The plurality of elastically deformable wires may be programmed with thermal memory. The plurality of elastically deformable wires may be programmed with superelasticity. The occluder may also include one or more anchors defined by one or more ends of the plurality of elastically deformable wires. The jacket may include dacron. The jacket may include polyurethane. The occluder may also include an occluding agent enclosed within the jacket. The occluding agent may include one or more threads of polyester. The occluder may also include an eye in operable relation to at least one of the clips, and the delivery system may also include a retrieval filament configured to engage the eye to retrieve the occluder. At least one of the clips may be an interdigitated clip. An end of the pushing catheter may be interdigitated and may be configured to removably interlock with the interdigitated clip. The system may also include a lumen defined through the occluder and the delivery system. The delivery system may also include a guide wire within the lumen and passing through an interior of the occluder. The delivery system may also include a stiffening catheter configured to engage at least one of the clips to compress the occluder.

In another aspect, the invention is a method for occluding an occlusion site. An occluder including a pair of clips configured in spaced relation, a plurality of elastically deformable wires secured by the clips and extending in arcuate conformation therebetween, and a jacket in operable relation to the plurality of elastically deformable wires is provided. A delivery system including a guiding catheter configured to receive the occluder and a pushing catheter configured to engage at least one of the pair of clips is provided. The guiding catheter is positioned adjacent the occlusion site. The occluder is positioned within the guiding catheter. At least one of the pair of clips is engaged with the pushing catheter. The occluder is slide relative to the guiding catheter with the pushing catheter so as to deploy the occluder from the guiding catheter so as to recover the arcuate conformation to occlude the occlusion site.

In other aspects, the occluder may also include one or more anchors defined by one or more ends of the plurality of elastically deformable wires, and the method may also include anchoring the occluder at the occlusion site with the one or more anchors. At least one of the clips may be an interdigitated clip, and an end of the pushing catheter may be interdigitated, and the method may also include retrieving the occluder by interlocking the interdigitated clip with the interdigitated end of the pushing catheter by drawing at least a portion of the occluder within the guiding catheter. The method may also include repositioning the occluder. The occluder and delivery system may also include an eye in operable relation to at least one of the clips and a retrieval filament configured to engage the eye, and the method may also include retrieving the occluder by drawing at least a portion of the occluder within the guiding catheter with the retrieval filament. The method may also include repositioning the occluder. The occluder may also include a lumen defined through the occluder and a guide wire configured to pass within the lumen, and the method may also include guiding the occluder toward the occlusion site with the guide wire. The delivery system may also include a stiffening catheter configured to engage at least one of the clips, and the method may also include engaging the at least one of the clips with the stiffening catheter and compressing the occluder with the stiffening catheter by increasing the distance between the pair of clips. The occlusion site may be a vascular occlusion site. The occlusion site may be a ureter occlusion site. The occlusion site may be a patent ductus arteriosus site.

In another aspect, the invention is a method for closure of patent ductus arteriosus having an aortic and pulmonary side. An occluder including a pair of clips configured in spaced relation, a plurality of elastically deformable wires secured by the clips and extending in arcuate conformation therebetween, and a jacket in operable relation to the plurality of elastically deformable wires is provided. A delivery system including a guiding catheter configured to receive the occluder and a pushing catheter configured to engage at least one of the pair of clips is provided. The guiding catheter is positioned adjacent the patent ductus arteriosus. The occluder is positioned within the guiding catheter. The occluder is deployed from the guiding catheter so as to recover the arcuate conformation to close the patent ductus arteriosus.

In other aspects, the occluder may also include a guide wire in operable relation to the guiding catheter, and the method may also include guiding the occluder toward the patent ductus arteriosus with the guide wire. The positioning may include positioning the occluder on the pulmonary side.

Other features and advantages of the disclosed method and apparatus will become apparent with reference to the following detailed description of embodiments thereof in connection with the accompanying drawings wherein like reference numerals have been applied to like elements, in which:

BRIEF DESCRIPTION OF THE DRAWINGS

FIG. 17 shows an occluder utilizing a stiffening catheter according to one embodiment of the presently disclosed method and apparatus.

FIG. 18 shows a detailed view of a guide wire, stiffening catheter, and occluder cap according to one embodiment of the presently disclosed method and apparatus.

DESCRIPTION OF ILLUSTRATIVE EMBODIMENTS

It will be appreciated that the presently disclosed method and apparatus provide for certain significant advantages. For instance, in one embodiment, the method and apparatus allow for occlusion that is faster than that of previous techniques. Achieving better coverage of a given occlusion site, the technique of this embodiment advantageously provides quick mechanical blockage of blood and induces thrombosis that leads to quick occlusion. The method and apparatus of this embodiment also advantageously provide a mechanism for self-anchoring occlusion. The self-anchoring, in turn, tends to greatly reduce or eliminate migration of the occlusion device and, hence, reduces or eliminates problems associated with migration.

Various embodiments of the disclosed method and apparatus offer further advantages. These advantages include ease of positioning and compactness. Specifically, the apparatus may easily achieve a 6-French size. Yet another advantage is repositionability. Because the presently disclosed occluder may be retrieved, it may be easily repositioned, and, hence, may provide for prompt correction of misplacements. Yet another advantage is guidewire compatibility, which facilitates navigation through a patient. The method and apparatus also advantageously provide safe, controllable occluder deployment with precise positioning capabilities. Such features make possible successful vascular, ureter, and patent ductus arteriosus closure.

Additionally, in one embodiment, the presently disclosed method and apparatus is suitable for transarterial approaches and especially for transvenous approaches. The design is adaptable to various PDA shapes and sizes. The length of the disclosed apparatus is still acceptable even when in an elongated state. These and other advantages will be made more clear with reference to the description below.

Figure 1:
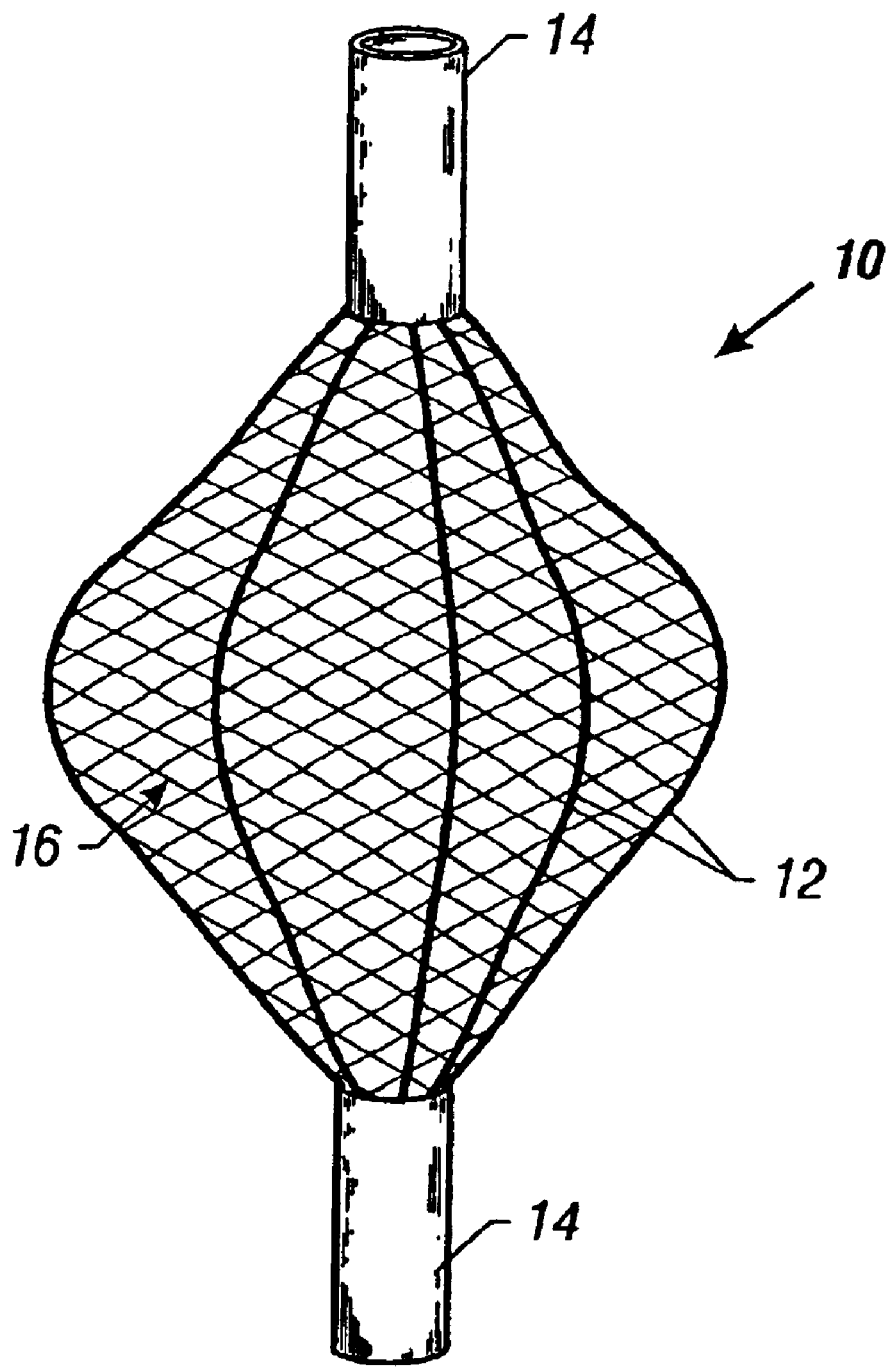
FIG. 1 shows an occluder according to one embodiment of the presently disclosed method and apparatus.

Turning first to FIG. 1, there is shown an occluder 10 according to one embodiment of the presently disclosed method and apparatus. Occluder 10 includes a pair of clips 14, a plurality of elastically deformable members 12, and a jacket 16. In operation, occluder 10 may be positioned at an occlusion site to mechanically block blood passage and to induce thrombosis.

Elastically deformable members 12 may be configured to assume an arc, or bowed shape, as shown in FIG. 1. Such a shape may facilitate occlusion, for an outer surface of elastically deformable members 12 may engage and press against an inner surface of an opening, firmly anchoring occluder 10 and creating a mechanical blockage of blood flow (see, e.g., FIG. 19). Elastically deformable members 12 may be configured so that they may be compressed upon application of a force so that they may be positioned within an opening without substantially engaging the inner surface of that opening (see, e.g., FIG. 5). For instance, when compressed, elastically deformable members 12 may be placed within a guiding catheter (see, e.g., FIG. 15) so that occluder 10 may be brought into position adjacent an occlusion site. Being compressible, elastically deformable members 12 may also be repositioned about or withdrawn from an occlusion site. Due to their elastic nature, elastically deformable members 12 may substantially recover their bowed shape upon removal of a force. In particular, elastically deformable members 12 may be made to resiliently spring back into a bowed shape to anchor occluder 10 when deployed from a constraining guiding catheter.

In one embodiment, elastically deformable members 12 may be made from any material suitable to become elastically deformed such that occluder 10 may be compressed and may thereafter substantially recover its original, uncompressed, arcuate shape. In one embodiment, elastically deformable members 12 may be nitinol wires, but, again, any other material suitable to exhibit elastic deformations as described herein may be substituted therewith. The number of elastically deformable members 12 may vary widely, but in one embodiment, the number of elastically deformable members 12 may be from four to six. The material making up elastically deformable members 12 may be chosen to exhibit biocompatibility suited for a particular application.

In one embodiment, elastically deformable members 12 may be secured in spaced relation with clips 14 and may assume an arcuate conformation between those clips. In the embodiment of FIG. 1, elastically deformable members 12 are secured in longitudinally spaced relation by being coupled at their ends to clips 14. In one embodiment, the coupling of elastically deformable members 12 to clips 14 may be accomplished by crimping. However, with the benefit of the present disclosure, those of skill in the art will understand that elastically deformable members 12 may be coupled to clips 14 by any suitable technique known in the art including, but not limited to, welding, gluing, taping, hooking within clips 14, interlocking with clips 14, clamping, or the like. In one embodiment, clips 14 may be made from stainless steel or nitinol, but any other suitable material may be utilized. Again, the material making up clips 14 may be chosen to exhibit an appropriate degree of biocompatibility.

Although shown in FIG. 1 as being secured at their ends, elastically deformable members 12 may be secured at other locations in other embodiments. For instance, in the embodiment of FIG. 8, to be described below, the securing of elastically deformable members 12 does not occur at the ends of elastically deformable members 12. Although the securing mechanism of the embodiment of FIG. 1 involves clips 14, other embodiments may provide securement by other means. For instance, other embodiments may secure elastically deformable members 12 by twisting their ends together or by tying or joining a filament or other suitable device about those ends. It is contemplated that many other alternative methods known in the art may be utilized to secure elastically deformable members 12. In one embodiment, elastically deformable members 12 may be made from 5 nitinol wires. Although the size of the wires may vary widely, in one embodiment, the diameters may range anywhere from about 0.006 to about 0.011 inches.

Figure 2:
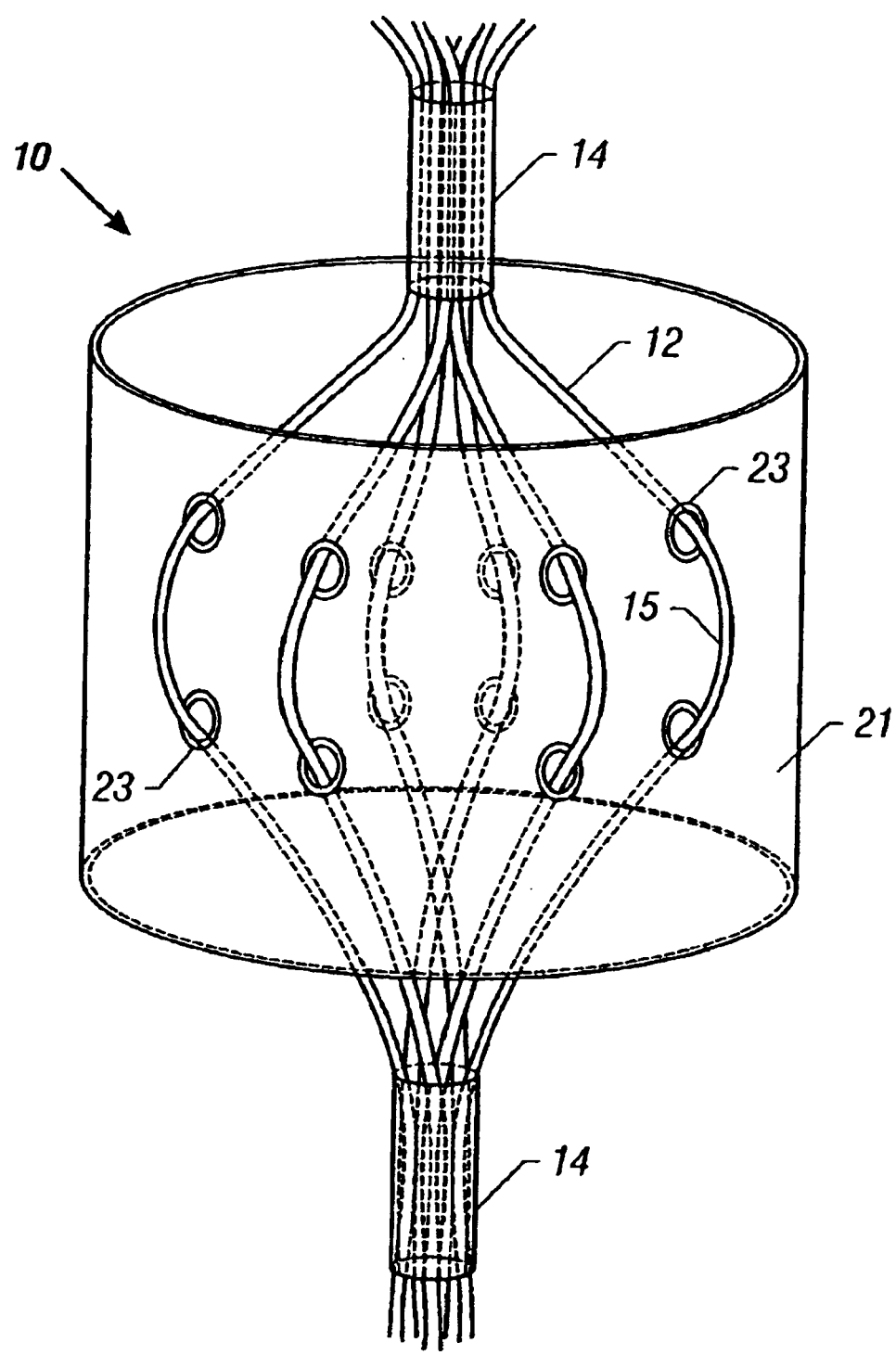
FIG. 2 shows an occluder being programmed with superelasticity or thermal memory according to one embodiment of the presently disclosed method and apparatus.
Figure 3A:
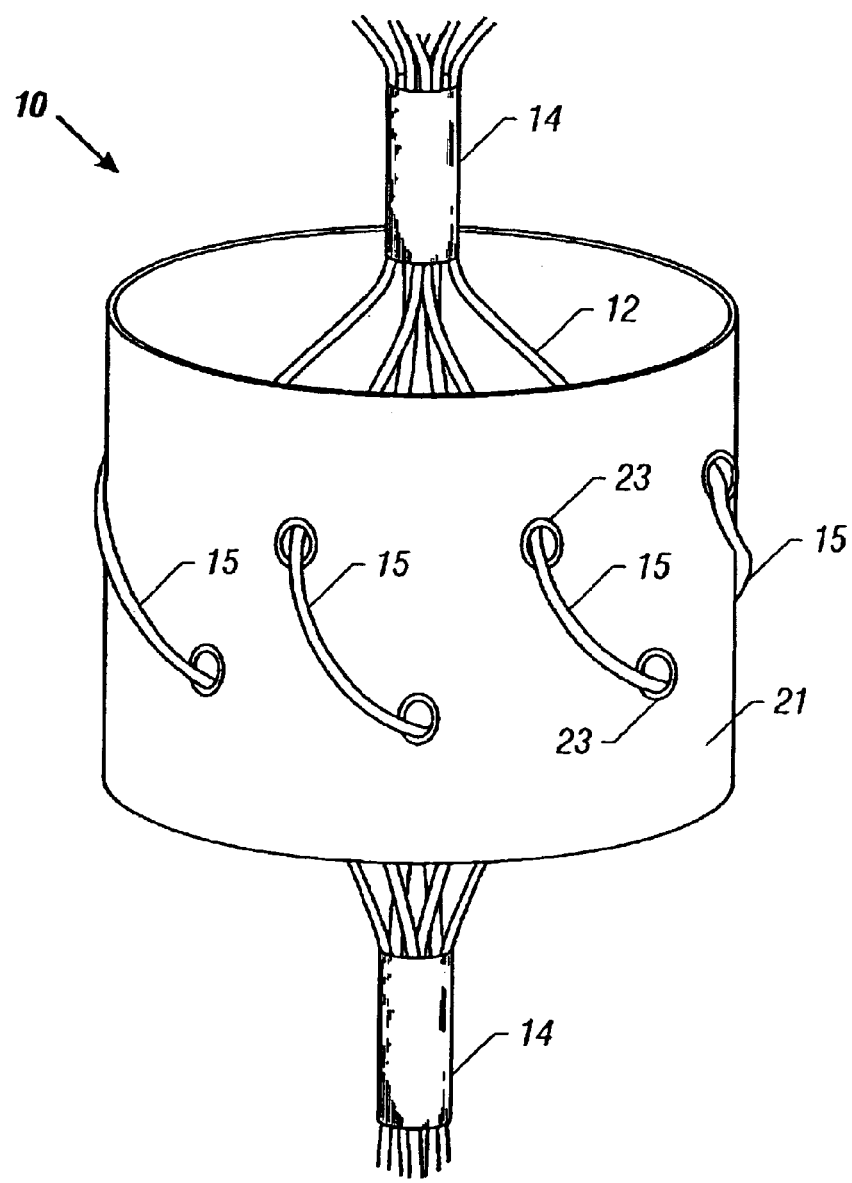
FIG. 3A shows an occluder being programmed with superelasticity or thermal memory according to another embodiment of the presently disclosed method and apparatus.
Figure 3B:
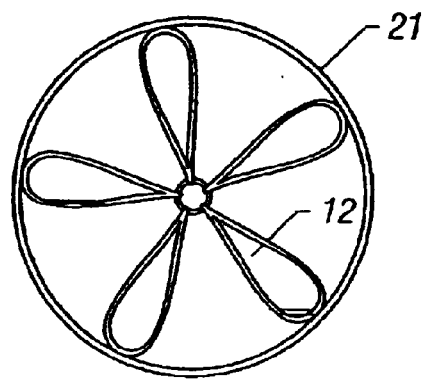
FIG. 3B shows a top view of an occluder being programmed according to one embodiment of the presently disclosed method and apparatus.
Figure 6:
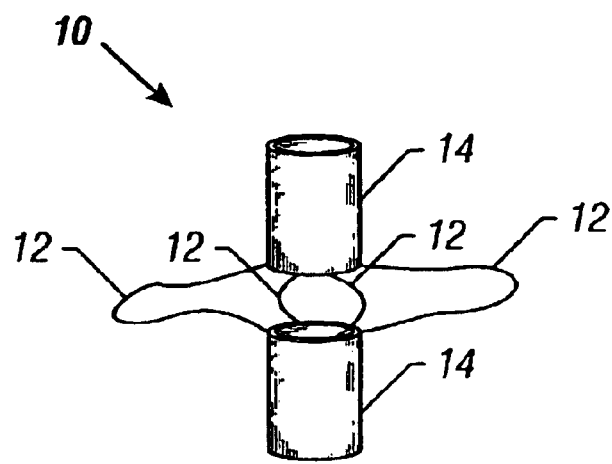
FIG. 6 shows an extended occluder according to one embodiment of the presently disclosed method and apparatus.

In one embodiment, elastically deformable members 12, such as nitinol wires, may be programmed with superelasticity or thermal memory as illustrated in FIG. 2, FIG. 3A, and FIG. 3B. In particular, they may be programmed to substantially recover an arcuate shape, such as the one shown in FIG. 1, upon removal of a compressing force. Programming of superelasticity or thermal memory may be accomplished by any one of a number of techniques known in the art. In one embodiment utilizing nitinol wires having a diameter ranging anywhere from about 0.006 to 0.011 inches, programming may be achieved by first forming a desired arcuate shape. For instance, spacing between clips 14 may be decreased such that a desirable arc shape is formed. To achieve an even more bowed shape (e.g., to achieve a flat disc configuration), clips 14 may be brought very close together as is shown in FIG. 6.

Having achieved a desired shape, elastically deformable members 12 may be secured into place by any suitable means. For instance, in one embodiment, elastically deformable members 12 may be securedly wrapped around a ring of material, such as copper, so that elastically deformable members 12 assume a desired arcuate shape. In the embodiment of FIG. 2, FIG. 3A, and FIG. 3B, portion 15 of elastically deformable members 12 may be secured to copper ring 21, used as a cylindrical template, by being threaded through holes 23 formed in the ring 21. It will be understood that the number and arrangement of holes 23 may vary according to the desired shape of elastically deformable members 12. In the illustrated embodiments, elastically deformable members 12 are threaded through adjacent holes 23 in ring 21 that surround the body of occluder 10. Being stretched so as to be threaded through the ring 21, elastically deformable members 12 may be made to form a desired arcuate shape. In one embodiment, holes 23 may be created parallel to the axis of ring 21 so that elastically deformable members 12 of occluder 10 may be arranged in planes that are perpendicular to the longitudinal axis of ring 21 (see FIG. 2). If holes 23 are arranged obliquely, elastically deformable members 12 of occluder 10 may be twisted (see FIG. 3A and FIG. 3B, FIG. 3B being a top view). It will be understood that any desirable shape may be formed in accordance with the present disclosure.

Being secured in place, elastically deformable members 12 may be exposed to heat for a certain period of time to complete the programming. In one embodiment, heat exposure may be about 500 degrees Celsius, and the exposure time period may be about 5 to about 15 min to achieve superelasticity or about 60 to about 120 min to achieve thermal memory. With programming complete, elastically deformable members 12 may easily be compressed to form a compressed-state occluder 10 (see, e.g., FIG. 5) at room temperature. With the benefit of the present disclosure, those of skill in the art will understand that different times and temperatures may be used to achieve programming of elastically deformable members 12. Also, it will be understood that other methods may be used to accomplish superelasticity or thermal memory, and it will also be understood that such programming is optional—elastically deformable members 12 made of appropriate elastic materials may be adapted to substantially recover an arcuate shape upon removal of a force naturally (i.e. without any need for heat or other types of programming).

Figure 15:
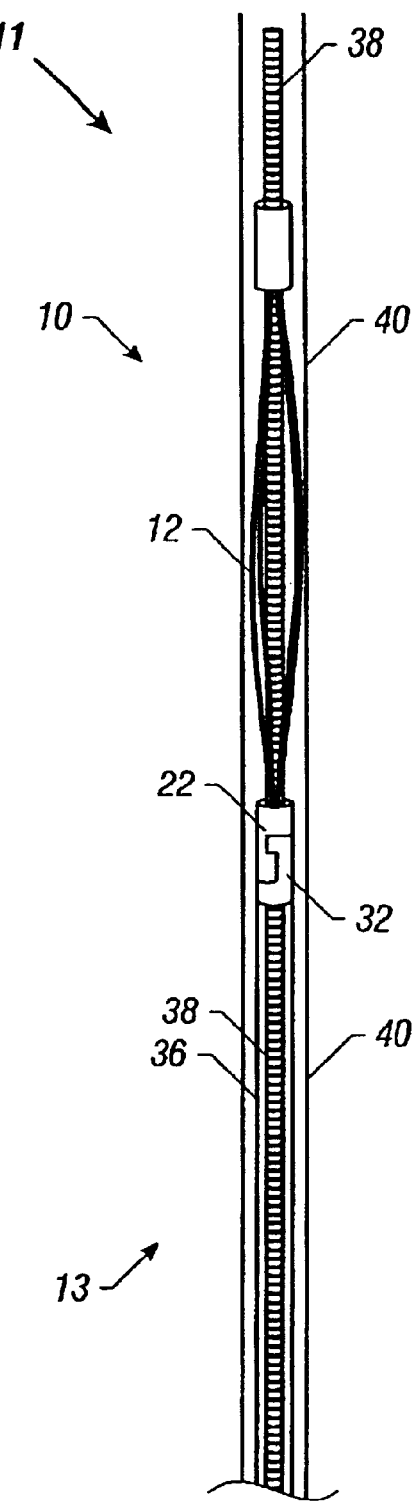
FIG. 15 shows a compressed occluder within a guiding catheter according to one embodiment of the presently disclosed method and apparatus.

In one embodiment, thermal shape memory may provide sufficient expansile force to prevent migration of occluder 10 within, for instance, a vessel. At room temperature, elastically deformable members 12 may easily be straightened for loading the occluder 10 into a lumen of a guiding sheath 40 (discussed in detail with reference to FIG. 12. FIG. 13, and FIG. 15). Again, although temperature dependent shape memory may be used for fabrication of the devices disclosed herein, similar functional characteristics may be achieved by utilizing non-temperature dependent properties of materials, and more particularly, the non-temperature dependent superelasticity of nitinol.

Configurations of occluders 10 described herein offer a wide range of geometrical variations. Lengths of occluders 10 may vary widely according to application, but in one embodiment, the length may be between about 17 and 29 mm. To create different occluder shapes, the distance between clips 14 (or other securing mechanisms) holding the wires together and the arrangement of elastically deformable members 12 may be altered. If the distance between clips 14 is decreased as much as possible (see, e.g., FIG. 6), four elastically deformable members 12 may form a four-leaf clover shape. Such an arrangement of elastically deformable members 12 may result in a flat-disc design. If the distance between clips 14 is increased, elastically deformable members 12 may form an oval or spherical basket. Due to its ability to take on different sizes and shapes, occluders 10 disclosed herein may advantageously occlude a wide variety of differently sized and shaped occlusion sites.

In one embodiment, elastically deformable members 12 may be arranged at approximately 90 degrees to each other, although it will be understood than any suitable other angle may be used. In one embodiment, elastically deformable members 12 may be parallel to one another in the mid-portion of occluder 10. Such a configuration may result in improved contact with a vessel wall and may provide better coverage within a vessel lumen. In one embodiment, elastically deformable members 12 may be configured in a spiral shape that may provide a more even distribution of members around the circumference of the occluder without requiring additional members.

In one embodiment, jacket 16 may be configured to cover at least a portion of elastically deformable members 12. Jacket 16 may facilitate the mechanical blockage of an occlusion site and may induce further thrombosis. Jacket 16 may be made of any material suitable to cover at least a portion of elastically deformable members 12, but in one embodiment, a woven material may be used. More particularly, in one embodiment a woven dacron material may be used as jacket 16. Such woven dacron may be particularly well suited for vascular and patent ductus arteriosus occlusion. In other embodiments, different material may be used, such as polyurethane. Polyurethane, or other impermeable materials, may be particularly well suited for ureter occlusion. In such an embodiment, a polyurethane jacket may have a thickness of about 0.002 inches, but it will be understood than any suitable thickness may be substituted therewith. In embodiments well suited for ureter occlusion, a suitable lubricant may be used to decrease the friction between jacket 16 and walls of a guiding catheter 40 (discussed with reference to FIG. 12, FIG. 13, and FIG. 14). In such embodiments utilizing polyurethane or impermeable jackets, the attachment of jacket 16 may need to be loosened so as to allow air to pass through occluder—otherwise, a vacuum may be formed within occluder 10, and the vacuum may prevent the complete opening of occluder 10 upon deployment.

In one embodiment, jacket 16 may be made to cover elastically deformable members 12 by pulling jacket 16 material over elastically deformable members 12 and attaching the material to crimping sites at, in, or near caps 14. Although any suitable attachment technique known in the art may be used, in one embodiment, jacket 16 is attached to a crimping site with 5-0 or 6-0 Prolene monofilament sutures.

Figure 4:
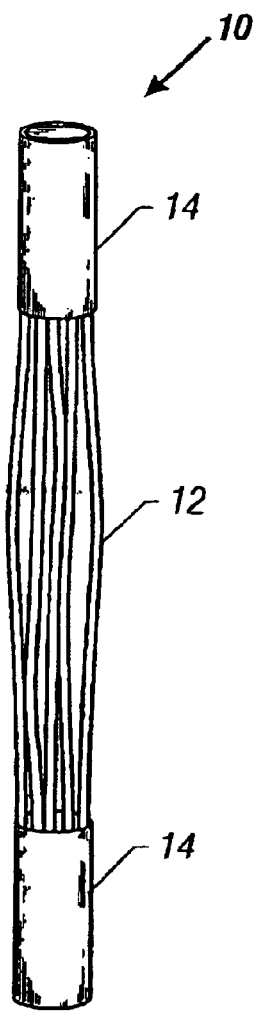
FIG. 4 shows an occluder in a semi-compressed state according to one embodiment of the presently disclosed method and apparatus.
Figure 5:
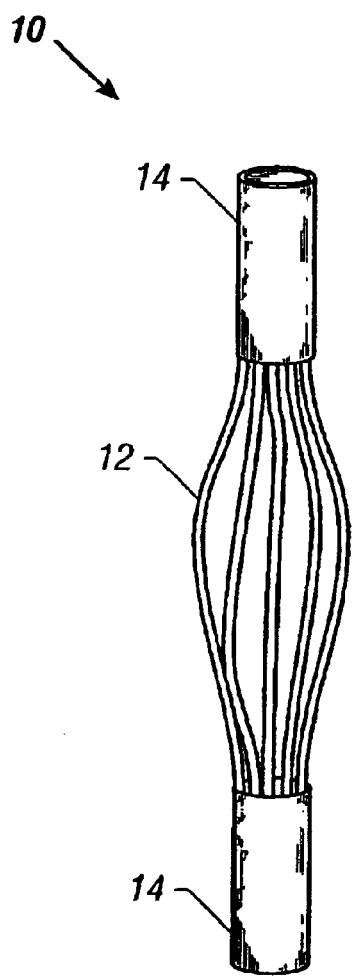
FIG. 5 shows an occluder in a compressed state according to one embodiment of the presently disclosed method and apparatus.

Turning now to FIG. 2, FIG. 3, and FIG. 4, there are shown occluders 10 in various stages of compression. FIG. 4 shows a snapshot of an occluder 10 in a semi-compressed state. In this state, occluder 10 may be resiliently rebounding to substantially recover its original arcuate shape or may be showing the first signs of being compressed. The shape of FIG. 4 may be seen, for instance, when an occluder 10 is only partially deployed from a guiding catheter, or when occluder 10 has begun to be retrieved from an occlusion site for repositioning. FIG. 5 shows an occluder 10 in a compressed state. As illustrated, elastically deformable members 12 may be substantially straight, extending longitudinally between secured positions, here secured by caps 14. In this state, occluder 10 may be positioned inside, for instance, a guiding catheter (see, e.g., FIG. 15). This position may be achieved through the application of a force to elastically deformable members 12. In particular, this configuration may be achieved through the application of one or more compression forces directed towards the interior of occluder 10. Such force, or compression forces, may be achieved with a guiding catheter whose inner surfaces exert compressing forces about outer surfaces of elastically deformable members 12. This configuration, or any compressed configuration, may also be achieved by increasing the distance between secured portions of elastically deformable members 12. For instance, by increasing the distance between caps 14, occluder 10 may be compressed. FIG. 6 shows an occluder 10 that is extended to a great degree. As illustrated, caps 14 may be brought very close together so that elastically deformable members 12 assume an exaggerated bow shape. Such a configuration may be useful for occluding a wide occlusion site. In one embodiment, an expansion ratio (diameter after delivery divided by constrained diameter within a guiding catheter) of an occluder 10 according to the present disclosure may be about 5.6 (unconstrained diameter being about 15 mm, constrained diameter within a 8-F ID sheath being about 2.7 mm).

Figure 7:
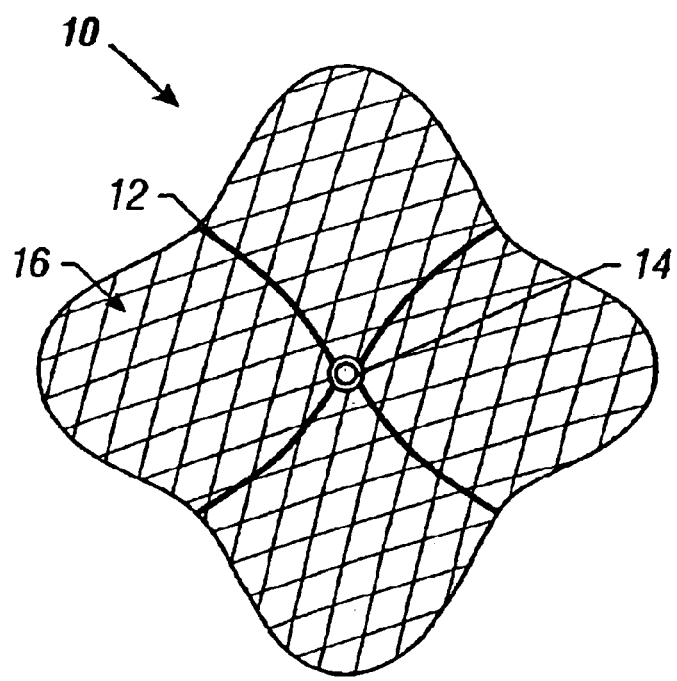
FIG. 7 shows a top view of an occluder according to one embodiment of the presently disclosed method and apparatus.

FIG. 7 shows a top view of an occluder 10. The shape of the top view depends, of course, upon the extent of compression of occluder 10 and the number of elastically deformable members 12. A top view corresponding to the fully compressed embodiment of FIG. 5 may be, for instance, nearly circular and thin. However, the top view of the embodiment illustrated in FIG. 6 may be shaped like a wide, exaggerated four-leaf clover. For embodiments such as those shown in FIG. 1 or FIG. 4, the shape may be similar to that shown in FIG. 7. As discussed previously, in all the embodiments described herein, the shape of occluder 10 may be modified greatly by adjusting the number of elastically deformable members 12 and by changing the arc shape to achieve the best occluding shape for a particular application. In particular, a wider occlusion site may require an occluder 10 such as the one shown in FIG. 6 while a more narrow site may necessitate an occluder 10 having only a slightly bowed shape.

Figure 8:
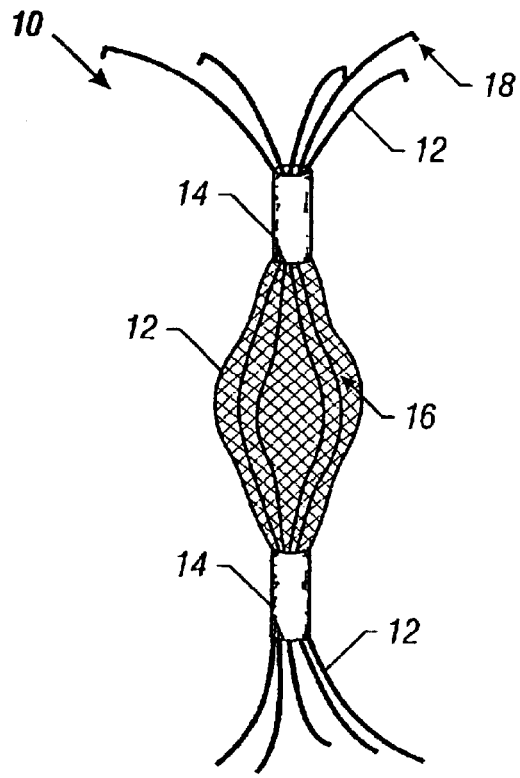
FIG. 8 is a side view of an occluder having anchors according to one embodiment of the presently disclosed method and apparatus.

Turning to FIG. 6, FIG. 7, FIG. 8, there are shown embodiments in which elastically deformable members 12 are not secured at their ends. In such embodiments, elastically deformable members 12 may be configured to extend beyond, for instance, clips 14 securing elastically deformable members 12. If no clips are used, elastically deformable members 12 may extend beyond the location in which securement is achieved. In the embodiment of FIG. 8, occluder 10 includes anchors 18 defined by elastically deformable members 12. Anchors 18 may be configured to further facilitate (in addition to the arcuate shape of occluder 10) anchoring to an occlusion site. Although many different formations may serve as anchors, the illustrated embodiments demonstrate that anchors 18 may comprise a bend in elastically deformable members 12. Specifically, outer ends of elastically deformable members 12 may be bent back at right angles (or any other suitable angles) in a way to point generally towards each other. As illustrated, only one side of elastically deformable members 12 may include anchors (in FIG. 6, FIG. 7, and FIG. 8 only the top half of occluders 10 have anchors). Although illustrated as integral anchors, anchors 18 may be separate anchors coupled to elastically deformable members 12 by any technique known in the art including, but not limited to, welding, gluing, tying, or the like.

Figure 9:
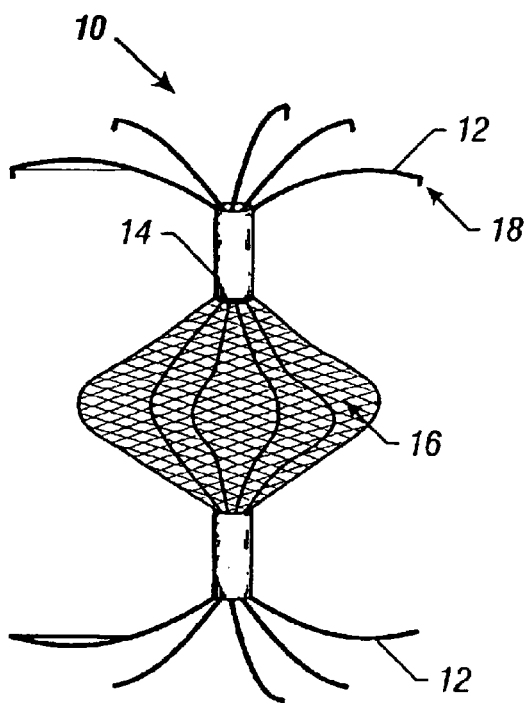
FIG. 9 is a side view of an extended occluder having anchors according to one embodiment of the presently disclosed method and apparatus.
Figure 10:
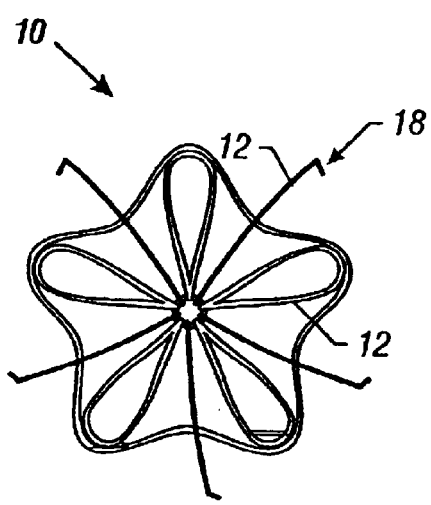
FIG. 10 is a top view of an occluder having anchors according to one embodiment of the presently disclosed method and apparatus.

FIG. 9 shows occluder 10 including anchors 18 in a semi-compressed state. As illustrated, the ends of elastically deformable members 12 may be configured to flex outward to cover a greater area and to better anchor occluder 10. FIG. 10 is a top view of an occluder having anchors 18 and demonstrates how the anchors may be spread relative to the body of occluder 10. Again, depending on the number of elastically deformable members 12 and the extent of its bow shape, the shape of occluder may vary widely. In the illustrated embodiment of FIG. 10, occluder 10 assumes a shape similar to a four leaf clover having smooth transitions from leaf to leaf.

Figure 11:
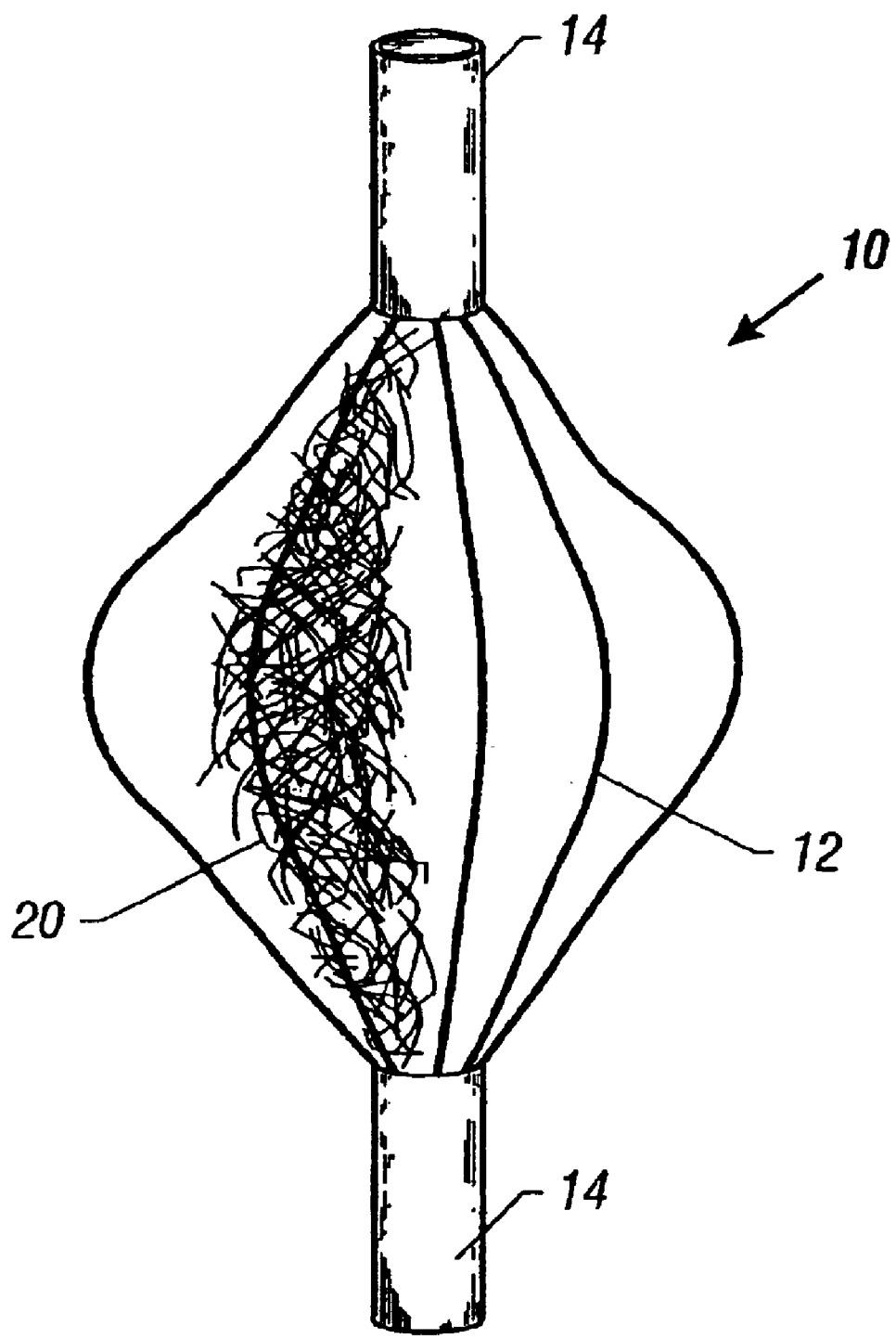
FIG. 11 shows an occluder including an occluding agent according to one embodiment of the presently disclosed method and apparatus.

Turning now to FIG. 11, there is shown an occluder 10 that includes an occluding agent 20. Occluding agent 20 may be configured to facilitate quicker occlusion by providing more sites for thrombosis to occur. In one embodiment, occluding agent 20 may be enclosed within jacket 16 of occluder 10. Any material suitable for facilitating occlusion may be utilized to serve as occluding agent 20. In one embodiment, one or more threads of polyester may be used. The size and shape of occluding agent 10 may be varied according to need. In one embodiment, only a few polyester fibers may be used as an agent, while in other embodiments, most or all of the interior of an occluder 10 may be filled with an occluding agent such as polyester threads. Occluding agent 20 may advantageously provide for immediate and complete closure, which, in turn, may prevent hemolysis and bacterial endocarditis.

With reference to FIGS. 10–16, the operation of the presently disclosed method and apparatus may be better understood. Looking first to FIG. 12, there is shown an occlusion apparatus 11 including an occluder 10 having a cap 14, elastically deformable members 12, an interdigitated cap 22 having recessed portion 26 and projecting portion 24, an eye 25, and a delivery system 13 having a pushing catheter end 32 that is interdigitated with a recessed portion 30 and a projecting portion 28, and a filament 27. Cap 14 and elastically deformable members 12 may be configured as described herein. Interdigitated cap 22 may be similar to cap 14 except for its shape. Interdigitated cap 22 may be interdigitated as illustrated or otherwise designed so that it may matingly engage a pushing catheter 32.

Figure 16:
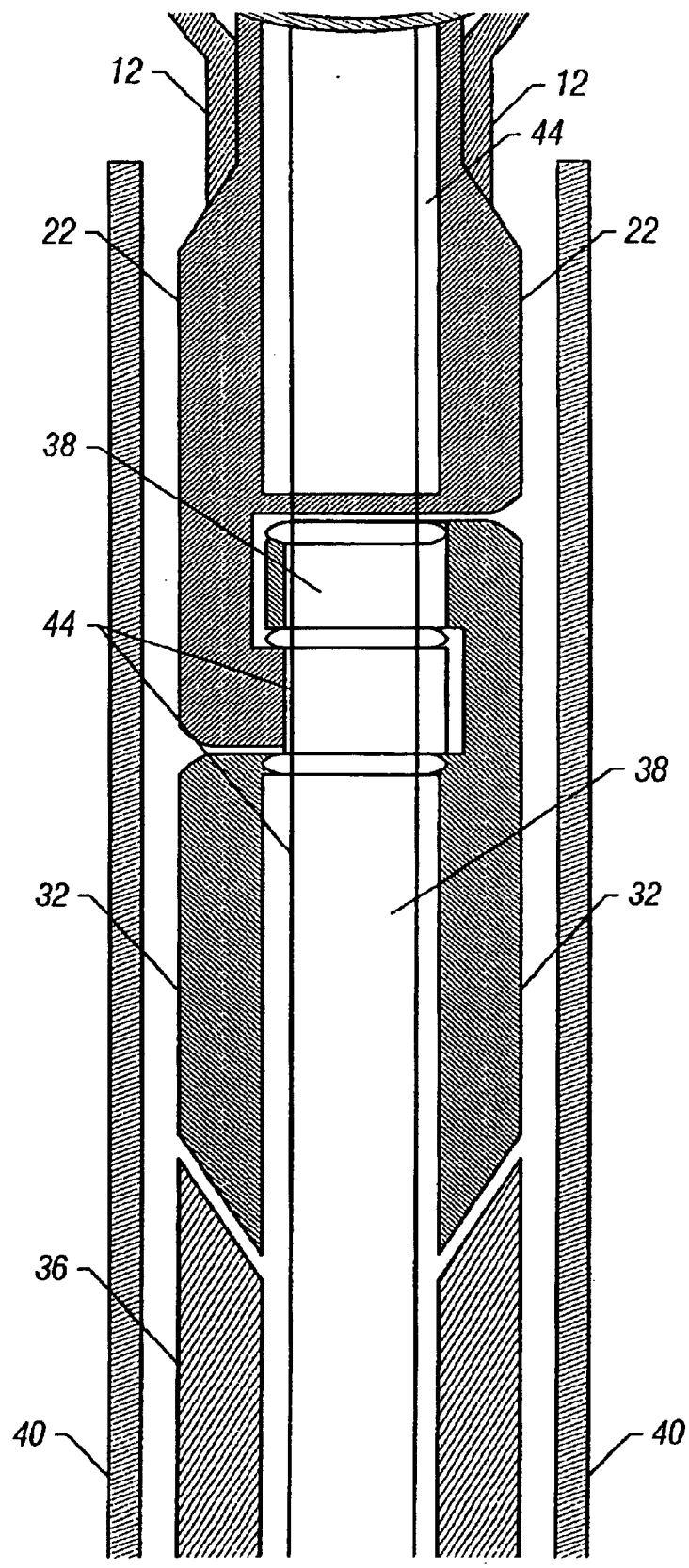
FIG. 16 shows a detailed view of a guide wire, a guiding catheter, and an interdigitated pushing catheter according to one embodiment of the presently disclosed method and apparatus.

In operation, pushing catheter end 32 may be interlocked with interdigitated cap 22 by inserting projecting portion 28 within recessed portion 26 and by correspondingly inserting projecting portion 24 within recessed portion 30 (see, e.g. FIG. 16 showing an interlocked arrangement). Once interlocked, occluder 10 may be pushed, or pulled by pushing catheter end 32 so that occluder 10 may be positioned, for instance, near an occlusion site. Such a feature advantageously allows for simple repositioning of occluder 10. In one embodiment, to release pushing catheter from occluder 10, pushing catheter end 32 may be lightly flexed laterally. The flexing may release the interlocking portions of cap 22 and pushing catheter end 32 so that occluder 10 may become free. The amount of flexing necessary to release occluder 10 may vary with application and may be lessened if occluder 10 is securely anchored to, for instance, the interior of a vessel With benefit of the present disclosure, it will be understood that any one of a number of other suitable interlocking techniques known in the art may be substituted for the one illustrated in FIG. 12 and FIG. 13. For example, pushing catheter end 32 may screw into cap 22 (or a cap such as cap 14) to provide for engagement. In other embodiments, pushing catheter end 32 and cap 22 (or cap 14) may be magnetic or electromagnet so that an attractive force (which may or may not be controllable by varying an electrical current) may be utilized to fix pushing catheter end 32 to cap 22 to allow for two-way positioning (forward and backwards) of occluder 10.

Although shown as exhibiting an interlocking relationship, those of skill in the art will understand, with benefit of the present disclosure, that interlocking or other mating design choices are optional. For instance, in one embodiment, pushing catheter end 32 may not be interdigitated and may be, for example, a smooth cylinder. To move occluder 10 in such an embodiment, pushing catheter end 32 may engage an end of cap 22 (or, a cap such as the cap 14) so that occluder 10 may be pushed into a proper position for occlusion. It will be understood that in such an embodiment, only one way positioning of occluder 10 may be possible.

Figure 12:
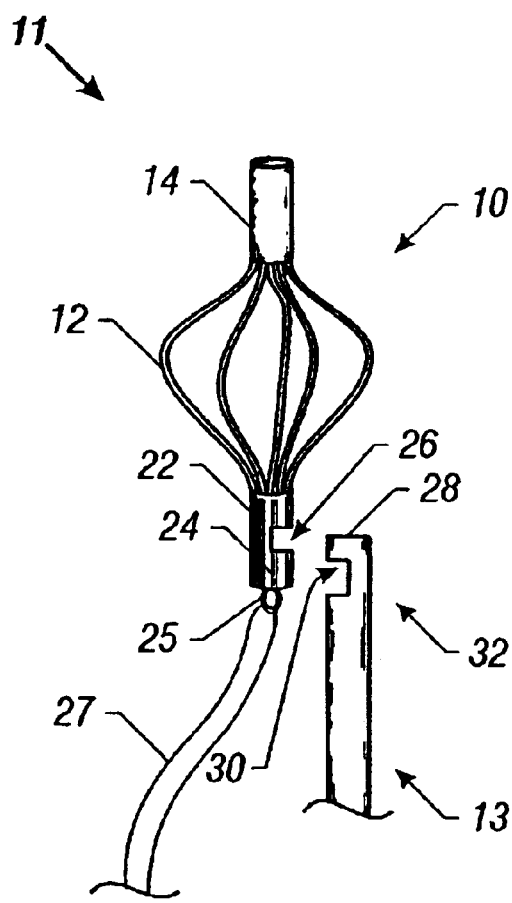
FIG. 12 shows an occluder having an interdigitated end corresponding to an interdigitated end of a pushing catheter according to one embodiment of the presently disclosed method and apparatus.
Figure 13:
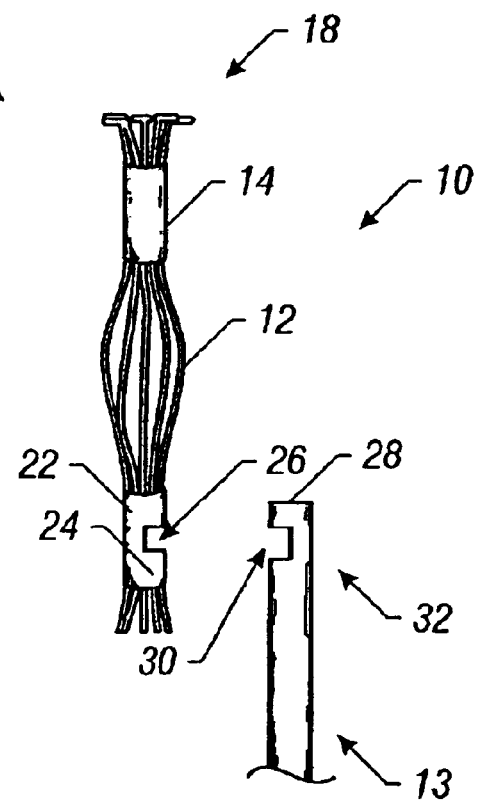
FIG. 13 shows an occluder having anchors and an interdigitated end corresponding to an interdigitated end of a pushing catheter according to one embodiment of the presently disclosed method and apparatus.

Eye 25 of occluder 10 of FIG. 12 may be configured to receive filament 27 so that occluder 10 may be retrieved even when no longer interlocked or associated with pushing catheter end 32. In particular, filament 27 may be pulled so that occluder 10 may be withdrawn even if occluder 10 has been released from pushing catheter end 32. As will be discussed below, such a feature advantageously allows for the repositioning of occluder 10.

FIG. 13 shows an occluder 10 and delivery system 13 similar in configuration to those of FIG. 12. The embodiment of FIG. 13 utilizes elastically deformable members 12 secured not at their ends and includes anchors 18 along an upper portion of elastically deformable members 12. Also, the embodiment of FIG. 13 does not contain an eye 25, although it will be understood that an eye may be added.

Figure 14:
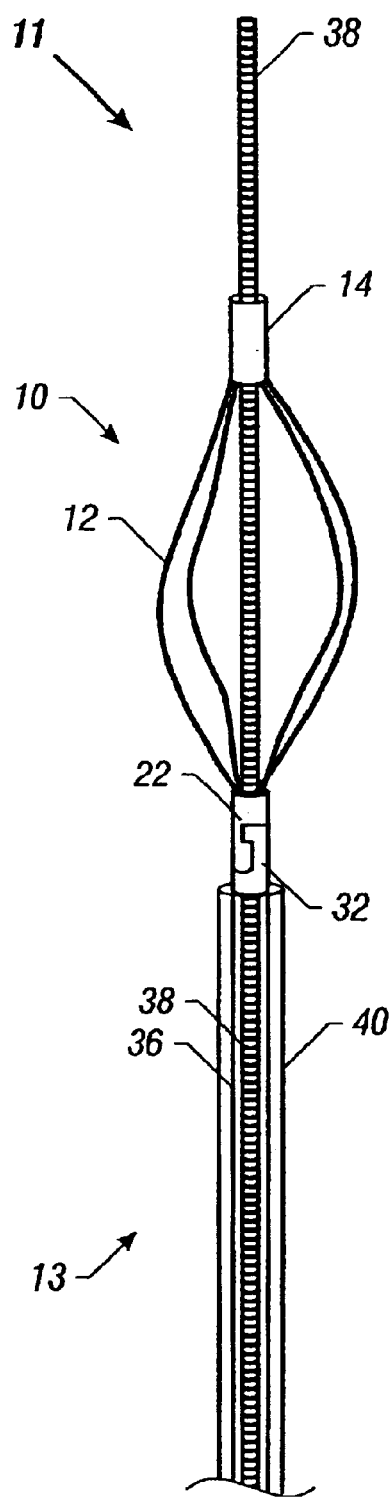
FIG. 14 shows a deployed occluder and guide wire according to one embodiment of the presently disclosed method and apparatus.

FIG. 14 shows an occluder 10 including a cap 14, elastically deformable members 12, and interdigitated cap 22. The delivery system 13 of FIG. 14 shows an interdigitated pushing catheter end 32, pushing catheter 36, guide wire 38, and guiding catheter 40. In this illustrated embodiment, a lumen runs through occluder 10 and delivery system 13. Within this lumen, guide wire 38 may pass. Guide wire 38 may be configured to guide occluder 10 during deployment from guiding catheter 40. In particular, guide wire 38 may assure that occluder 10 travels in a straight line to a desired occlusion site. Although it may be made of any suitable material, in one embodiment, guide wire 38 may be constructed from nitinol or stainless steel. Guide wire 38 may have a size that varies widely, but in one embodiment, it may be 0.018-inches to 0.035-inches. In one embodiment, the surface of guide wire 38 may be treated to modify the coefficient of sliding friction between, for instance, cap 14 and guide wire 38. The friction may be modified to make sliding along guide wire 38 easier or more difficult, depending upon the desired result. Additionally, guide wire 38 may be ratcheted so that, for example, the precise motion of occluder 10 may be controlled ratchet by ratchet With benefit of the present disclosure, those of skill in the art will recognize that guide wire 38 may be configured differently to steer occluder 10 through sliding engagement.

Guiding catheter 40 may be configured to enclose occluder 10 when in a compressed-state, as shown in FIG. 15. There, it may be seen that inner walls of guiding catheter 40 may exert a pressure upon an outer surface of elastically deformable members 12, causing compression into a substantially linear state (see also FIG. 5). In the compressed-state, occluder 10 may be guided within guiding catheter 40 to reach, for instance, an occlusion site. The size and materials of guiding catheter 40 may vary widely according to application, but in one embodiment, guiding catheter 40 may be constructed of Teflon and may be about 6-French to 8-French OD in diameter.

Shown also in FIG. 12 and FIG. 13 is pushing catheter 36. In one embodiment, and as mentioned earlier, pushing catheter 36 may be configured to engage occluder 10 to move, or slide, occluder 10 relative to guiding catheter 40. In one embodiment, the engagement may be through an interdigitated pushing catheter end 32 configured to interlockingly mate with cap 22. In such an embodiment, motion of occluder 10 relative to guiding catheter 40 may be two ways—thus, occluder 10 may be deployed or partially deployed by moving occluder 10 forward (i.e. upward in FIG. 12 and FIG. 13) and occluder 10 may be retrieved (and perhaps subsequently repositioned) by sliding occluder 10 backward (i.e. downward in FIG. 12 and FIG. 13). In other embodiments, motion of occluder 10 from pushing catheter 36 may be one way. In such an embodiment, pushing catheter end 32 may be flat or shaped such that engagement with cap 22 (or a cap such as cap 14) may not be interlocking or may not be stable in more than one direction. The size and materials of pushing catheter 36 may vary widely according to application, but in one embodiment, guiding catheter 36 may be constructed of Teflon, nylon, or any suitable material and may be 4-French to 6-French OD in diameter.

In one embodiment, pushing catheter 36 may be replaced by a superelastic nitinol microtubing of similar size with a lumen that may accept a suitable guide wire. In such an embodiment, end 32 may be attached to the distal end of the superelastic nitinol microtubing by any suitable means, and an interdigitating engagement may be created between end 32 and cap 22. In yet another embodiment, an integral end 32 may be created as a contiguous portion of a superelastic nitinol microtubing.

Turning to FIG. 16, there is shown a more detailed view of a portion of a delivery system 13 according to one embodiment of the present disclosure. As illustrated, a guide wire 38 passes through a lumen 44 extending through delivery system 13. In this embodiment, cap 22 is matingly engaging pushing catheter end 32 via interlocking interdigitated surfaces. Pushing catheter 36 may be seen to have a shape suitable for engaging end 32. In particular, in the illustrated embodiment, pushing catheter 36 is angled corresponding to an angled surface of end 32. In this embodiment, pushing catheter 36 is separate from end 32, and, thus, movement of occluder 10 may be limited to one way motion within guiding catheter 40. However, in other embodiments, pushing catheter 36 may be integral with end 32 and may be arranged so that two way motion of occluder 10 may be utilized.

Turning to FIG. 17, there is shown an embodiment of an occluder apparatus utilizing a stiffening catheter 46. In this embodiment, stiffening catheter 46 may be configured to slide relative to guide wire 38. In particular, stiffening catheter 46 may slidably engage an outer surface of guide wire 38. In operation, stiffening catheter 46 may engage an end stop 48 of a cap 14 to increase the distance between caps 14 to compress occluder 10, as may be better seen with reference to FIG. 18. In FIG. 18, it may be seen that cap 14 may include a lumen allowing for passage of guide wire 38. The lumen may be narrowed, however, by an end stop 48, which may be integral with cap 14 or may be coupled thereto by any suitable means known in the art. As illustrated, stiffening catheter 46 may be sized so that it may slide relative to guide wire 38, but it may not slide past end stop 48. Rather, stiffening catheter 46 may be slid to contact, and engage end stop 48. Upon engagement, stiffening catheter 46 may be pushed so that the distance between caps 14 may be increased. Increasing that distance may lead to the generation of compression forces tending to compress occluder 10 into a thinner configuration. Stiffening catheter 46 may thus be used to withdraw a deployed or partially deployed occluder 10 back into, for instance, a guiding catheter 10 so that it may be repositioned at a different occlusion site.

In the embodiment of FIG. 17, it may be seen that occluder 10 and delivery system 13 may be equipped with an eye 25 coupled to a filament 27. In one embodiment, eye 25 and filament 27 may be used to further increase the distance between caps 14 to further compress occluder 10. For instance, filament 27 may be pulled while stiffening catheter 46 may be advanced. In such a manner, lower cap 14 may be drawn downward (relative to the illustration of FIG. 15 and FIG. 16) while upper cap 14 may be advanced upward (relative to the illustration of FIG. 15 and FIG. 16)—thus, the distance between caps 14 may be increase so as to compress occluder 10.

Figure 19:
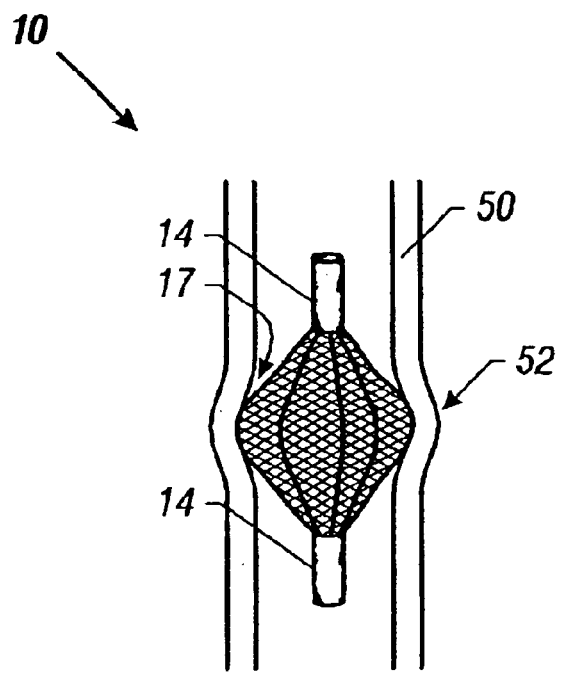
FIG. 19 is a side view of an occluder occluding an occlusion site according to one embodiment of the presently disclosed method and apparatus.

With reference to FIG. 19, it may seen how occluder 10 may be used for occluding an occlusion site, the location of which is indicated generally by arrow 17. In one embodiment, occluder 10 may be brought to occlusion site 17 by first being compressed into a compressed state, such as the state illustrated in FIG. 5. In such a state, occluder 10 may be enclosed within a guiding catheter 40, as illustrated in FIG. 15. It is contemplated that walls of guiding catheter 40 may serve as the compressing mechanism. In other words, occluder 10 may be inserted into guiding catheter 40, and the walls of guiding catheter may exert inward forces upon occluder 10, causing occluder 10 to become compressed so that it may fit within guiding catheter 40.

Once within guiding catheter 40, occluder 10 may be positioned adjacent occlusion site 17. As used here, by "adjacent", it is meant that occluder 10 may be positioned in an appropriate location for carrying out the occlusion process. In one embodiment, positioning of occluder 10 may be facilitated through the use of a guide wire 38 illustrated in FIGS. 12–16. In particular, guide wire 38 may be used to precisely locate occlusion site 17. With guide wire 38 in place, occluder 10 may be deployed along the guide wire, thus ensuring an accurate deployment. Once in position, occluder 10 may be slid relative to guiding catheter 40 so that it may be released. As has been disclosed herein, the sliding may be accomplished by engaging a cap 14 of occluder 10 with a pushing catheter end 32, attached or coupled to a pushing catheter 36, as shown in, e.g., FIG. 16. As occluder 10 is slid further, it will eventually exit guiding catheter 40. While so being deployed, occluder 10, due to its elastic nature, will recover its arcuate conformation. In particular, as the force from the walls of guiding catheter 40 is removed, elastically deformable members 12 recover their original, bowed shaped, a shape illustrated, for example, in FIG. 1. Again, in one embodiment, occluder 10 may still be coupled to guide wire 38, even after deployment. In such an embodiment, occluder 10 may use guide wire 38 to lead a direct path to occlusion site 17. Once securely located at site 17, guide wire 38 may be removed by sliding guide wire 38 relative to occluder 10 until guide wire 38 no longer engages occluder 10. Guide wire 38 may then be removed from the area, by, in one embodiment, riding within guiding catheter 40.

Once fully deployed, occluder 10 may occlude occlusion site 17, as shown, for instance, in FIG. 19. FIG. 19 illustrates, generally, a vascular occlusion, but with the benefit of the present disclosure those of skill in the art will understand that the present disclosure is not limited vascular occlusion, but rather may be used for any occlusion application including, but not limited to, ureter occlusions, and the occlusion of patent ductus arteriosus. As illustrated, deployed occluder 10, having an arcuate shape, may bias (via an anchoring force) vessel walls 50 to cause a bulge 52. In one embodiment, good fixation of occluder 10 within a vessel lumen may correspond with a situation in which the greatest unconstrained diameter of an occluder 10 is about 25%–33% larger than that of the recipient vascular segment, although it is contemplated that other relative size percentages will also suffice to properly anchor occluder 10. It is also contemplated that such percentages may depend heavily upon the conditions of the site being occluded, and may thus vary widely according to application.

Figure 20:
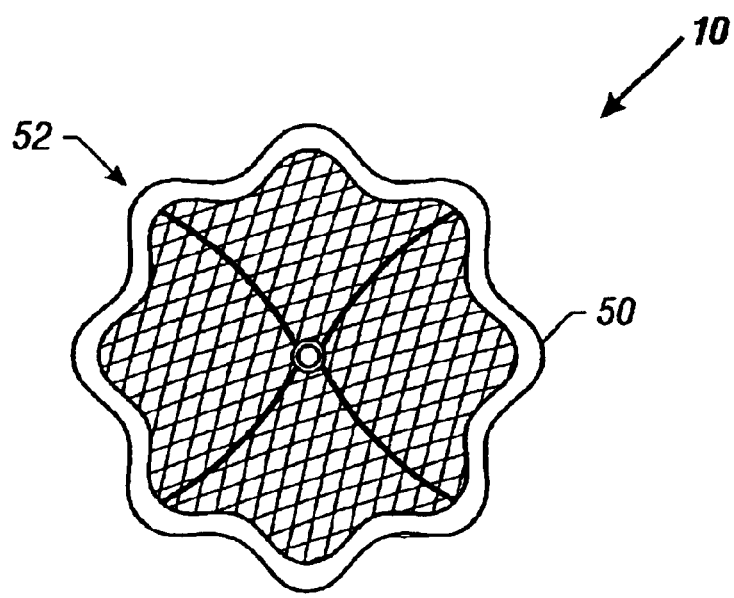
FIG. 20 is a top view of an occluder occluding an occlusion site according to one embodiment of the presently disclosed method and apparatus.

The biasing of walls 50 may lead to the secure anchoring of occluder 10 within the vessel (or, generally, opening) so that migration may be reduced or eliminated. FIG. 20 shows a top view of occluder 10 anchored at occlusion site 17. As illustrated, outer surfaces of elastically deformable members 12 may conform to substantially match the shape of walls 52. Further, it may be seen that the elastic nature of elastically deformable members 12 may exert an outward anchoring force that manifests itself as an outward bulge 52. Again, such an anchoring force may reduce or eliminate migration, and therefore, may reduce or eliminate several problems associated with migration of occluding devices. For instance, the presently disclosed method and apparatus may provide for occlusion that is more permanent in nature reducing the number of return trips a patient must make to a hospital.

Although not illustrated in FIG. 19, the use of anchors 18 (see, e.g., FIG. 6, FIG. 7, and FIG. 8) may further increase the anchoring of occluder 10, for anchors 18 may grip walls 50 and decrease the chance of any unwanted migration from occlusion site 17. Although not illustrated in FIG. 19, occluder 10 may be equipped with an occluding agent 20, as shown in FIG. 11. In one embodiment, occluding agent 20 may include one or more polyester threads, in the form of fuzzy fibers or even forming a bundle that provide additional sites for thrombosis—the additional sites may facilitate quicker occlusion of occlusion site 17, which may, in turn, ensure more precise occlusion at occlusion site 17.

If occlusion may be completed rapidly, there may be a reduced probability that occluder 10 will migrate during the occlusion process. In other words, quick occlusion may itself contribute to quick, successful anchoring of occluder 10. Quick occlusion has several advantages including a lower probability of distal embolization. If occlusion is taking place too slowly, fragments of soft, fresh thrombi may break off and be carried away with the still-not-arrested blood flow distally to an intended occlusion site. In high flow conditions (e.g., a-v fistulas, patent ductus arteriosus), partial occlusion may result in hemolysis, which is related to the persistent turbulent flow through the device and which can be a source of complications.

In embodiments described herein, occluders 10 may optionally be retrievable and repositionable to correct for misplacement errors or to more accurately position an occluder at a specific location. In one embodiment, occluder 10 may be retrieved and repositioned through the use of interdigitated cap 22 and matching interdigitated pushing catheter end 32, as illustrated, for instance, in FIGS. 10–14. In such an embodiment, pushing catheter 36 may exert bidirectional forces upon occluder 10 via its interlocked coupling with interdigitated cap 22. As disclosed previously, and as will be appreciated by those of skill in the art, it is contemplated that other mechanisms may serve to bi-directionally couple pushing catheter 36 to occluder 10 other than interdigitating ends, but for convenience the following discussion assumes an interdigitated technique. In this embodiment, pushing catheter 36 may push and pull occluder 10 within guiding catheter 40 (see FIG. 15).

With reference to FIG. 14, it may be seen how this design may provide for retrieval and repositionability. In FIG. 14, occluder 10 has been deployed from guiding catheter 40, but has not been released from pushing catheter 36. In particular, pushing catheter end 32 is still interlocked with interdigitated end 22 of occluder 10. In such a position, an operator may release or retrieve occluder 10. In one embodiment, the shaft of pushing catheter 36 may be marked to note the position at which interdigitated end 22 will become free of guiding sheath 40—such a mark may prevent premature or unexpected deployment of occluder 10.

To release occluder 10, an operator may slightly flex pushing catheter 36 so as to fully release occluder 10 at an occlusion site (as disclosed earlier, a slight flexing motion may release the interlocking hold of pushing catheter 36 upon occluder 10 by briefly separating the interlocking recesses and projecting portions of end 32 and cap 22). To retrieve, an operator may pull pushing catheter 36 so as to retrieve occluder 10 by withdrawing at least a portion of occluder 10 back into guiding catheter 40. When retrieving, the walls of guiding catheter 40 may exert inward forces upon elastically deformable members 12 so that at least a portion of occluder 10 may become compressed and may fit within guiding catheter 40. Within, or partially within, guiding catheter 40, occluder 10 may be repositioned as desired.

In another embodiment, occluder 10 may be retrieved by using eye 25 and filament 27 as illustrated in FIG. 10 and FIG. 15. Although not shown, those of skill in the art will recognize that eye 25 may be eliminated by threading filament 27 through cap 14 or by attaching filament 27 in another suitable manner, or to another suitable location upon occluder 10. In one embodiment, occluder 10 may be partially or fully withdrawn back into guiding catheter 40 by pulling on filament 27. This embodiment advantageously allows for retrieval (and repositioning) of occluder 10 even after occluder 10 has been fully deployed and released from pushing catheter 36, for filament 27, coupled to occluder 10 by eye 25, may be pulled even after pushing catheter 36 has been withdrawn back into guiding catheter 40. In one embodiment, if retrieval or repositioning is not desired, filament 27 may be removed from eye 25 by cutting filament 27 and by withdrawing it from eye 25. In other embodiments, cutting may not be necessary—one end of filament 27 may simply be pulled so as to unthread eye 25.

In one embodiment, both an eye/filament technique and an interlocking pushing catheter technique may be used in combination to facilitate retrieval and repositioning. Additionally, stiffening catheter 46 (see FIG. 15 and FIG. 16) may be utilized in any of the disclosed embodiments to aid in retrieval and/or repositioning. In one embodiment, stiffening catheter 46 may be advanced to engage end stops 48 so as to compress occluder 10. The compression of occluder 10 may, in turn, simplify the withdrawal of occluder 10 back into guiding catheter 40 during a retrieval and/or repositioning procedure.

Turning to FIG. 19 and FIG. 20, there is shown a particular application for the presently disclosed method and apparatus—closure of patent ductus arteriosus. FIG. 19 and FIG. 20 show the anatomy of patent ductus arteriosus. In particular, an aortic arch 66 having a bracheocephalic artery 72, a left carotid artery 70, a left subclavian artery 68, a left pulmonary artery 62, and a descendent aorta 64 may be seen. Patent ductus arteriosus (PDA), illustrated by arrow 60 refers to the condition, well known in the art, of an abnormal persistence of an open lumen between the descendent aorta and the pulmonary artery. The direction of blood flow is directed from the aorta (higher pressure) to the pulmonary artery resulting in recirculating of arterial blood through the lungs as well as pulmonalis arterial hypertension.

Figure 21:
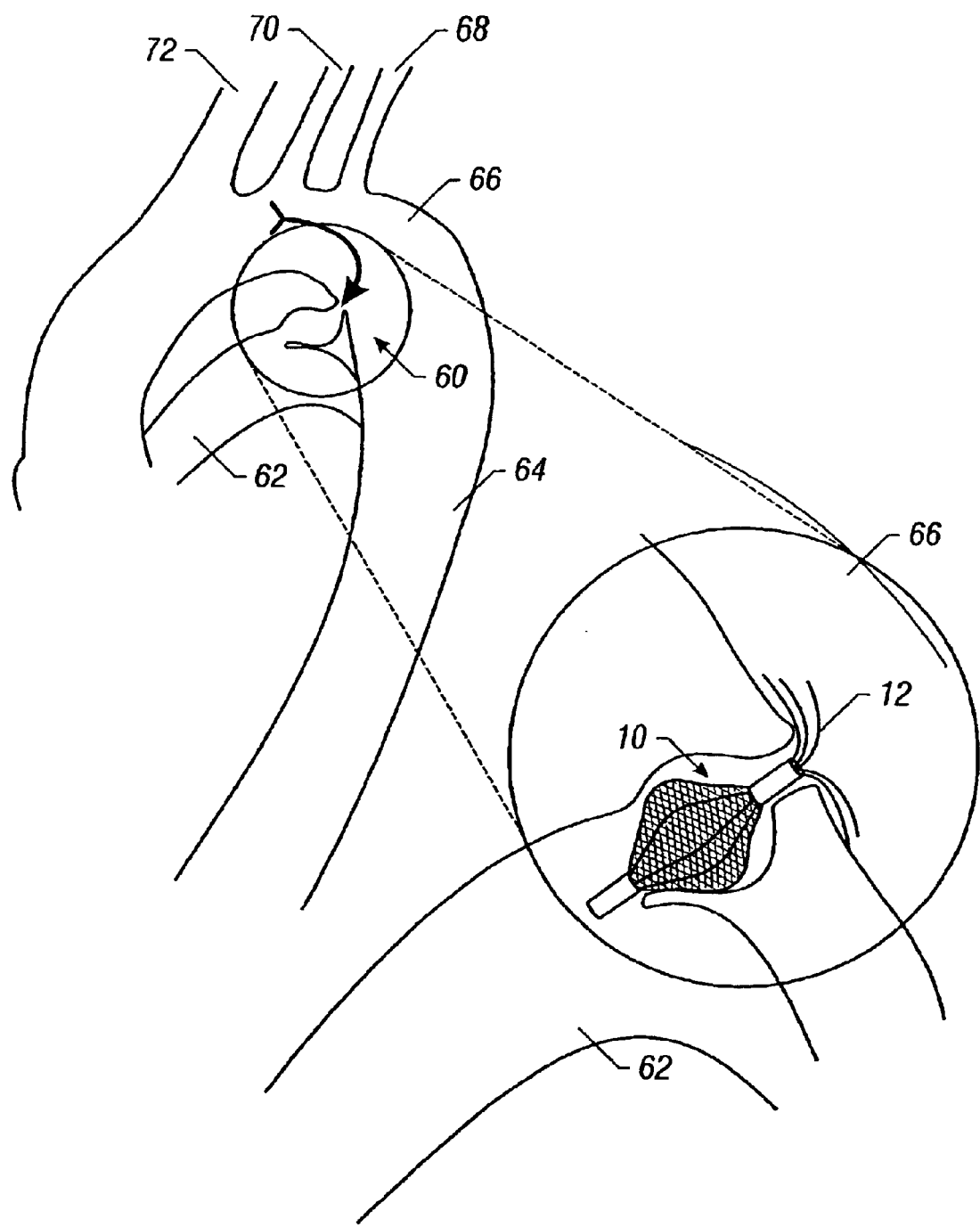
FIG. 21 shows an occluder closing a patent ductus arteriosus according to one embodiment of the presently disclosed method and apparatus.

In FIG. 21, PDA 60 may be closed using an occluder 10 in accordance with any of the embodiments of the present disclosure, and more particularly with an embodiment utilizing a guide wire 38. Occluder 10 may be positioned adjacent an occlusion site corresponding to PDA 60. Occluder 10 may be deployed (and retrieved and repositioned) so that occlusion may occur. In one embodiment, a guide wire 38 may aid in the precise deployment of occluder 10. In one embodiment, a femoral vein approach may be utilized in which occluder 10 may be deployed from the pulmonary artery 62. In the embodiment of FIG. 21, it may be seen that elastically deformable members 12 may form legs that may be deployed before the body of occluder 10. These legs may be equipped with anchors 18 to further aid in anchoring occluder 10. In one embodiment, legs may be arranged around a circumference of an aortic ostium. However, it will be understood that an occluder 10 without legs, such as the occluder 10 illustrated in FIG. 1, may likewise be used to close PDA 60.

Figure 22:
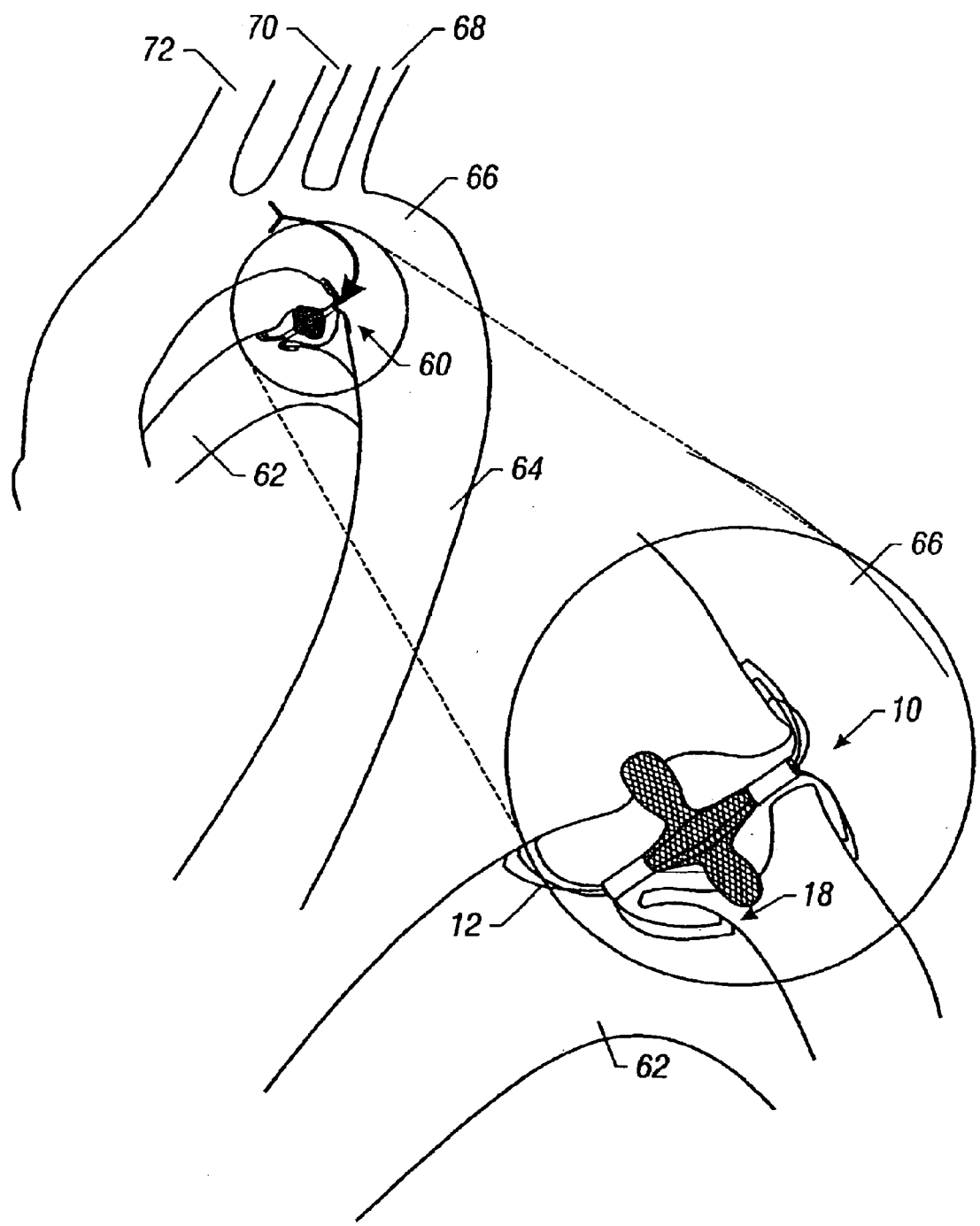
FIG. 22 shows an occluder with anchors closing a patent ductus arteriosus according to one embodiment of the presently disclosed method and apparatus.

In FIG. 22, PDA 60 may be closed with an occluder 10 having elastically deformable members 12 extending from both sides of the body of occluder 10 and having anchors 18. The legs and anchors 18 may aid in securely anchoring occluder 10 about PDA 60. As discussed above, in one embodiment, occluder 10 may be deployed from pulmonary artery 62. In both the embodiments of FIG. 19 and FIG. 20, those of skill in the art will recognize that size and shape of occluder 10 may be modified so as to best fit PDA 160.

With the benefit of the present disclosure, those of skill in the art will understand that the applications for the method and apparatus described herein are vast. For example, the disclosed occluders may be used in veins and non tapered vascular territories where the possibility of migration is high. High flow vascular lesions including arterio-venous malformations and fistulas may be one of the possible applications of the occluders both in lesions of the extremities and the lungs.

Chronic pseudoaneurysms may also be safely excluded from the circulation using the occluders described herein. Occluders described herein may also play a role in the non-surgical management of patients with systemic to pulmonary collateral vessels and shunts. The same holds true for the embolization treatment of coronary artery fistulas.

The occluders may also be used for embolization without migration on the venous side (e.g, for the treatment of varicoceles, or of aberrant vessels). This indication is supported by the fact that the detachable balloons are not recommended to be used for this purpose any longer.

As mentioned earlier, the presently disclosed method and apparatus may be particularly well suited for ureter occlusion. In particular, the presently disclosed occluders may cause a prompt and reliable ureteral occlusion without the need for injecting other embolic agent(s) to complete the obstruction. Migration of the device may be prevented by the self anchoring mechanism, and the occluder may be made in a repositionable form. From a technological and economical viewpoint, the disclosed occluders are also advantageous in that they may also be used for vascular occlusion. In fact, the only difference between the two applications may be covering material of the jacket.

The following examples are included to demonstrate specific embodiments of the invention. It should be appreciated by those of skill in the art that the techniques disclosed in the examples which follow represent techniques discovered by the inventors to function well in the practice of the invention, and thus can be considered to constitute specific embodiments for its practice. However, those of skill in the art should, in light of the present disclosure, appreciate that many changes can be made in the specific embodiments which are disclosed and still obtain a like or similar result without departing from the spirit and scope of the invention.

EXAMPLES

To achieve quick, limited-size vascular occlusion, a self-expanding, self-anchoring basket-shaped vascular occlusion device has been designed and fabricated. Studies have been performed demonstrating occluders 10 in accordance with the present disclosure in a high-flow arterial model.

Device Construction

Devices of varying size have been constructed from four 0.009 inch nitinol wires held together at each end by a stainless steel clip. Nitinol, an alloy composed of 55% nickel and 45% titanium with a titanium-oxide layer, has been used because of its shape memory properties and established biocompatibility (Liu and Stice, 1990; Castleman et al., 1976). The disclosed occluder configuration has been achieved by pushing the two ends of the wire frame toward each other and then heating the device to 500° C. for 120 min. After allowing the device to cool to room temperature, a bead of silver solder was placed around each steel clip for reinforcement.

An elastic Dacron jacket, formed by heat sealing the edges, has been pulled over the metallic frame and attached at one end to the steel clip with 5-0 Prolene monofilament suture (Ethicon, Sommerville, N.J.). Small bundles of polyester threads have been placed within the Dacron jacket before attaching the open end to the other steel clip. In smaller occluders, polyester threads have been twisted together to form a compact bundle centered within the nitinol frame. In occluders used for aortic occlusion, polyester threads have formed a loose bundle that filled the space within the Dacron jacket.

Animal Testing

Three occluders that did not contain polyester threads were placed in the common iliac arteries of 2 domestic pigs (one device per artery). Subsequently, 14 devices containing polyester threads were placed in 10 common iliac arteries and 4 abdominal aortas of 5 domestic pigs.

The animals were fasted for 18 h before each procedure. Each pig was sedated with an i.m. injection of solution containing ketamine hydrochloride (15 mg/kg), acepromazine (0.15 mg/kg), and atropine sulfate (0.04 mg/kg). Anesthesia was induced with isofluorane (5%) administered via a mask. Once the pig was anesthetized, an endotracheal tube was inserted and anesthesia was maintained with isofluorane (1.5%), nitrous oxide (0.3 L/min), and oxygen (0.8 L/min).

A carotid artery was surgically isolated, an 8-F Flexor sheath (Cook Inc., Bloomington, Ind.) was introduced through a small arteriotomy, and sodium heparin (100 IU/kg) was given. Under fluoroscopic monitoring, the sheath was positioned in an iliac artery or the infrarenal portion of the abdominal aorta and angiography was performed through the sheath. An occluder was loaded into a 10.5-F OD stainless steel metal cartridge and then pushed from the cartridge directly into the previously placed Flexor sheath with the stiff end of an 0.052 inch guidewire equipped with a 0.092 inch guidewire piece. The occluder was advanced to the end of the sheath with the dilator, and while holding the dilator against the occluder, the sheath was withdrawn releasing the occluder into the vessel.

Hand injections of contrast were made under fluoroscopic observation at one minute intervals to determine the time required for complete vascular occlusion. When complete obliteration of the vascular lumen was seen fluoroscopically, an arteriogram was obtained to confirm the occlusion.

One hour after placement, the animal was sacrificed with an intravenous overdose (1.0 ml/10 lb of body weight) of Beuthanasia D (Schering-Plough Animal Health Corp.; Kenilworth, N.J.), and a complete necropsy was performed.

Results

The occluders were easy to deliver with good precision. Deployment of the occluders was smooth and continuous; none jumped from the end of the sheath when released. The occluders readily assumed their pre-programmed unconstrained diameter, and symmetrical positioning of the occluders was achieved in all but one case. One occluder placed in an aorta opened asymmetrically because the clip at one end failed to hold the nitinol wires together without movement.

Radiographically, the three occluders lacking polyester threads produced only partial vascular occlusion after one hour. Placement of the occluders containing polyester threads resulted in complete vascular occlusion of all iliac arteries and three of four abdominal aortas. The time required for complete common iliac occlusion was 2–8 min (median 5 min). Complete aortic occlusion occurred in 8, 13, and 16 min. respectively. Sixty minutes after deployment of the device that opened asymmetrically, only partial aortic occlusion was noted.

Necropsy revealed firm contact between the occluder and the vessel wall in all cases indicating effective anchoring of the device. The presence of firm contact was corroborated grossly by multiple indentations on the luminal surface caused by the nitinol wires.

Soft clot was found on the Dacron jackets of all occluders. A small amount of thrombus was found on the inside of the Dacron covering in the devices that did not contain polyester threads. A large amount of compact clot was found within the jacket of each basket containing threads. In some vessels, additional soft clot of limited size was also observed adjacent to the cephalad and/or caudad ends of the occluder.

While the present disclosure may be adaptable to various modifications and alternative forms, specific embodiments have been shown by way of example and described herein. However, it should be understood that the present disclosure is not intended to be limited to the particular forms disclosed. Rather, it is to cover all modifications, equivalents, and alternatives falling within the spirit and scope of the disclosure as defined by the appended claims. For instance, the disclosed apparatus may utilize different orientations of components, sizes of components, or materials according to needs. Moreover, the different aspects of the disclosed methods and apparatuses may be utilized in various combinations and/or independently. Thus the invention is not limited to only those combinations shown herein, but rather may include other combinations. In other words, those of skill in the art should, in light of the present disclosure, appreciate that many changes can be made in the specific embodiments that are disclosed and still obtain a like or similar result without departing from the spirit and scope of the invention.

REFERENCES

The following references, to the extent that they provide exemplary procedural or other details supplementary to those set forth herein, are specifically incorporated herein by reference.

Bing, Hicks, Figenshau, Wick M, Picus D, Darcy M D, Clayman R V. "Percutaneous ureteral occlusion with use of Gianturco coils and gelatine sponge, Part I. Swine model" *JVIR;* 3:313–317,1992 (a)

Bing, Hicks, Picus, Darcy. "Percutaneous ureteral occlusion with use of Gianturco coils and gelatine sponge, Part II. Clinical Experience," *JVIR;* 3:319–321, 1992(b)

Cambier, Kirby, Wortham, Moore, "Percutaneous closure of the small (<2.5 mm) patent ductus arteriosus using coil embolization," *Am. J. Cardiol.*, 69:815–816, 1992.

Castleman, Motzkin, Alicandri, Bonawit, "Biocompatibility of nitinol alloy as an implant material," *J. Biomed. Mater. Res.*, 10:695 731, 1976.

Dutton, Jackson, Hughes et al., "Pulmonary arteriovenous malformations: results of treatment with coil embolization in 53 patients," *AJR*, 165:1119 1125, 1995.

Furuse, Iwasaki, Yoshino, Konishi, Kawano, Kinoshita, Ryu, Satake, Moriyama, "Hepatocellular carcinoma with portal vein tumor thrombus: embolization of arterioportal shunts," *Radiology*, 204:787 790, 1997.

Gianturco, Anderson, Wallace, "Mechanical device for arterial occlusion," *AJR*, 124:428 435, 1975.

Grifka, Vincent, Nihill, Ing, Mullins, "Transcatheter patent ductus arteriosus closure in an infant using the Gianturco Grifka vascular occlusion device," *Am. J. Cardiol.*, 78:721 723, 1996.

Guglielmi, Vinuela, Duckwiler, Dion, Stocker, "Highflow, small-hole arteriovenous fistulas: treatment with electro-detachable coils," *AJNR*, 16:325 328, 1995.

Hendrickx, Orth, Grunert, "Long-term survival after embolization of potentially lethal bleeding malignant pelvic turnouts," *Br. J. Radial.*, 68:1336 1343, 1995.

Hijazi and Geggel, "Results of anterograde transcatheter closure of patent ductus arteriosus using single or multiple Gianturco coils," *Am. J. Cardiol.*, 74:925 929, 1994.

Hijazi and Geggel, "Transcatheter closure of patent ductus arteriosus using coils," *Am. J. Cardiol.*, 79:1279 1280, 1997.

Hosking, Benson, Musewe, Dyck, Freedom, "Transcatheter occlusion of the persistently patent ductus arteriosus," *Circulation*, 84:2313–2317, 1991.

Kónya, Wright, Wallace, "Anchoring coil embolization in a high-flow arterial model," *JVIR*, 9:249 254,1998.

Krichenko, Benson, Burrows, Moes, McLaughlin, Freedom, "Angiographic classification of the isolated, persistently patent ductus arteriosus and implications for percutaneous catheter occlusion," *Am. J. Cardiol.*, 63:877 880, 1989.

Latson, "Residual shunts after transcatheter closure of patent ductus arteriosus," *Circulation*, 84:2591 2593, 1991.

Levey, Teitelbaum, Finck, Pentecost, "Safety and efficacy of transcatheter embolization of axillary and shoulder arterial injuries," *JVIR*, 2:99 104, 1991.

Liu and Stice, "Shape memory alloys and their applications," *J. Appl. Manufact. Sys.*, 3:65 72, 1990.

Lloyd, Fedderly, Mendelsohn, Sandhu, Beekman, "Transcatheter occlusion of patent ductus arteriosus with Gianturco coils," *Circulation*, 88:1412 1420, 1993.

Magal, Wright, Duprat, Wallace, Gianturco, "A new device for transcatheter closure of patent ductus arteriosus: a feasibility study in dogs," *Invest. Radiol.*, 24:272 276, 1989.

Marks, Chee, Liddel, Steinberg, Panahian, Lane, "A mechanically detachable coil for the treatment of aneurysms and occlusion of blood vessels," *AJNR*, 15:821 827, 1994.

Masura, Walsh, Thanopoulous, Chan, Bass, Gousous, Gavora, Hijazi, "Catheter closure of moderate to large sized patent ductus arteriosus using the new Amplatz duct occluder: immediate and short term results," *J. Am. Coll. Cardiol.*, 31:878 882, 1998.

Menachem, Coldwell, Young, Burgess, "Hemorrhage associated with pelvic fractures: causes, diagnosis, and emergent management," *AJR*, 157:1005 1014, 1991.

Nancarrow, Fellows, Lock, "Stability of coil emboli: an in vitro study," *Cardiovasc. Intervent. Radiol.*, 10:226 229, 1987.

O'Halpin, Legge, MacErlean, "Therapeutic arterial embolization: report of five years' experience," *Clin. Radiol.*, 354:85 93, 1984.

Pozza, Gomes, Qian, Ambrozaitis, Kim, Amplatz, "Transcatheter occlusion of patent ductus arteriosus using a newly developed self-expanding device: evaluation in a canine model," *Invest. Radiol.*, 30:104 109, 1995.

Punekar, Prem, Ridhorkar, Deshmukh, Kelkar, "Post-surgical recurrent varicocele: efficacy of internal spermatic venography and steel-coil embolization," *Br. J. Urol.*, 77:12–128, 1996.

Rashkind, Mullins, Hellenbrand, Tait, "Nonsurgical closure of patent ductus arteriosus: clinical application of the Rushkind PDA occluder system," *Circulation*, 75:583–592, 1987.

Reidy and Qureshi, "Interlocking detachable platinum coils, a controlled embolization device: early clinical experience," *Cardiovasc. Intervent. Radiol.*, 19:85 90, 1996.

Sagara, Miyazono, Inoue, Ueno, Nishida, Nakajo, "Recanalization after coil embolotherapy of pulmonary arteriovenous malformations: study of long term outcome and mechanism for recanalization," *AJR*, 170:727 730, 1998.

Schild, Mildenberger, Kerjes, "Effectiveness of platinum wire microcoils for venous occlusion: a study on patients treated for venogenic impotence," *Cardiovasc. Intervent. Radiol.*, 17:170 172, 1994.

Schmitz Rode, Timmermans, Uchida, Kichikawa, Hishida, Gunther, Rosch, "Self-expandable spindle for transcatheter vascular occlusion: in vivo experiments," *Radiology*, 188:95 100, 1993.

Schwartz, Teitelbaum, Kantz, Pentecost, "Effectiveness of transcatheter embolization in the control of hepatic vascular injuries," *JVIR*, 4:359 365, 1993.

Selby Jr., "Interventional radiology of trauma," *Radiol. Clin. N. Am.*, 30:427 439, 1992.

Sharaffuddin, Gu, Cervera Ceballos, Urness, Amplatz, "Repositionable vascular occluder: experimental comparison with standard Gianturco coils," *JVIR*, 7:695 703, 1996.

Sharafuddin, Gu, Titus, Sakinis, Pozza, Coleman, Cervera-Ceballos, Aideyan, Amplatz, "Experimental evaluation of a new self expanding patent ductus arteriosus occluder in a canine model," *JVIR*, 7:877 887, 1996.

Sommer, Gutierrez, Lai, Parness, "Use of preformed nitinol snare to improve transcatheter coil delivery in occlusion of patent ductus arteriosus," *Am. J. Cardiol.*, 74:836 839, 1994.

Teitelbaum, Reed, Larsen, Lee, Pentecost, Finck, Katz "Microcatheter embolization of non-neurologic traumatic vascular lesions," *JVIR*, 4:149 154, 1993.

Tometzki, Arnold, Peart et al., "Transcatheter occlusion of the patent ductus arteriosus with Cook detachable coils," *Heart*, 76:531 535, 1996.

"Transcatheter occlusion of persistent arterial duct." Report of the European Registry, Lancet, 340:1062 1066, 1992.

Uzun, Hancock, Parsons, Dickinson, Gibbs, "Transcatheter occlusion of the arterial duct with Cook detachable coils: early experience," *Heart*, 76:269 273, 1996.

Vedantham, Goodwin, McLucas, Mohr, "Uterine artery embolization: an underused method of controlling pelvic hemorrhage," *Am. J. Obstet Gynecol.*, 176:938 948, 1997.

Wallace, Granmayeh, deSantos, Murray, Romsdahl, Bracken, Jonsson, "Arterial occlusion of pelvic bone tumors," *Cancer*, 43: 322 328, 1979.

Wessel, Keane, Parness, Lock, "Outpatient closure of the patent ductus arteriosus," *Circulation*, 77:1068 1071, 1988.

White, Pollak, Wirth, "Pulmonary arterivenous malformations: diagnosis and transcatheter embolotherapy," *JVIR*, 7:787 804, 1996.

Zubillaga, Guglielmi, Vinuela, Duckwiler, "Endovascular occlusion of intracranial aneurysms with electrically detachable coils: correlation of aneurysm neck size and treatment results," *AJNR*, 15:815820, 1994.

What is claimed is:

1. A method for occluding an occlusion site, comprising:
   providing an occluder including a pair of clips configured in spaced relation, a plurality of elastically deformable members secured by said clips and extending in arcuate conformation therebetween such that one or more of said members do not cross any other member, and a jacket covering the entire portion of said plurality of elastically deformable members extending in arcuate conformation;
   providing a delivery system including a guiding catheter configured to receive said occluder and a pushing catheter configured to engage at least one of said pair of clips;
   positioning said guiding catheter adjacent said occlusion site, wherein said occluder is positioned within said guiding catheter;
   engaging at least one of said pair of clips with said pushing catheter; and
   sliding said occluder relative to said guiding catheter with said pushing catheter so as to deploy said occluder from said guiding catheter so as to recover said arcuate conformation to occlude said occlusion site.

2. The method of claim 1, wherein said occluder further comprises one or more anchors defined by one or more ends of said plurality of elastically deformable members, and wherein said method further comprises anchoring said occluder at said occlusion site with said one or more anchors.

3. The method of claim 1, wherein at least one of said clips is an interdigitated clip, wherein an end of said pushing catheter is interdigitated, and wherein the method further comprises retrieving said occluder by interlocking said interdigitated clip with said interdigitated end of said pushing catheter by drawing at least a portion of said occluder within said guiding catheter.

4. The method of claim 3, further comprising repositioning said guiding occluder.

5. The method of claim 1, wherein said occluder and delivery system further comprise an eye in operable relation to at least one of said clips and a retrieval filament configured to engage said eye, and wherein said method further comprises retrieving said occluder by drawing at least a portion of said occluder within said guiding catheter with said retrieval filament.

6. The method of claim 5, further comprising repositioning said occluder.

7. The method of claim 1, wherein said occluder further comprises a lumen defined through said occluder and a guide wire configured to pass within said lumen, and wherein said method further comprises guiding said occluder toward said occlusion site with said guide wire.

8. The method of claim 1, wherein said delivery system further comprises a stiffening catheter configured to engage at least one of said clips, and wherein said method further comprises engaging said at least one of said clips with said stiffening catheter and compressing said occluder with said stiffening catheter by increasing the distance between said pair of clips.

9. The method of claim 1, wherein said occlusion site is a vascular occlusion site.

10. The method of claim 1, wherein said occlusion site is a ureter occlusion site.

11. The method of claim 1, wherein said occlusion site is a patent ductus arteriosus site.

12. A method for closure of patent ductus arteriosus having an aortic and pulmonary side, comprising:
    providing an occluder including a pair of clips configured in spaced relation, a plurality of elastically deformable members secured by said clips and extending in arcuate conformation therebetween such that one or more of said members do not cross any other member, and a jacket covering the entire portion of said plurality of elastically deformable members extending in arcuate conformation;
    providing a delivery system including a guiding catheter configured to receive said occluder and a pushing catheter configured to engage at least one of said pair of clips;
    positioning said guiding catheter adjacent said patent ductus arteriosus, wherein said occluder is positioned within said guiding catheter; and
    deploying said occluder from said guiding catheter so as to recover said arcuate conformation to close said patent ductus arteriosus.

13. The method of claim 12, wherein said occluder further comprises a guide wire in operable relation to said guiding catheter, and wherein said method further comprises guiding said occluder toward said patent ductus arteriosus with said guide wire.

14. The method of claim 12, wherein positioning comprises positioning said occluder on said pulmonary side.

* * * * *